US007740833B2

(12) United States Patent
Proudfoot et al.

(10) Patent No.: US 7,740,833 B2
(45) Date of Patent: Jun. 22, 2010

(54) THERAPEUTIC USES OF CHEMOKINE VARIANTS

(75) Inventors: Amanda Proudfoot, Chens sur Leman (FR); Jeffrey Shaw, Vessy (CH); Zoe Johnson, Slough (GB)

(73) Assignee: Merck Serono SA, Coinsins, Vaud (CH)

( * ) Notice: Subject to any disclaimer, the term of this patent is extended or adjusted under 35 U.S.C. 154(b) by 770 days.

(21) Appl. No.: 10/573,625

(22) PCT Filed: Oct. 18, 2004

(86) PCT No.: PCT/EP2004/052572

§ 371 (c)(1),
(2), (4) Date: Mar. 9, 2007

(87) PCT Pub. No.: WO2005/037305

PCT Pub. Date: Apr. 28, 2005

(65) Prior Publication Data

US 2007/0280958 A1    Dec. 6, 2007

(30) Foreign Application Priority Data

Oct. 16, 2003 (EP) .................................. 03078308

(51) Int. Cl.
  *A61K 45/00* (2006.01)
  *A61K 39/00* (2006.01)
  *A61K 38/60* (2006.01)
  *A01N 37/18* (2006.01)

(52) U.S. Cl. ............... 424/85.1; 424/185.1; 424/192.1; 424/198.1; 514/2; 530/324

(58) Field of Classification Search .................. None
See application file for complete search history.

(56) References Cited

U.S. PATENT DOCUMENTS

| 5,705,360 | A | * | 1/1998 | Rollins et al. | ............... 435/69.1 |
| 5,739,103 | A | | 4/1998 | Rollins et al. | |
| 5,993,814 | A | * | 11/1999 | Williams et al. | ......... 424/145.1 |
| 6,100,387 | A | * | 8/2000 | Herrmann et al. | .......... 536/23.4 |
| 6,617,135 | B1 | * | 9/2003 | Gillies et al. | ............... 435/69.7 |

FOREIGN PATENT DOCUMENTS

| WO | WO 03/083059 | 10/2003 |
| WO | WO 03/084993 | 10/2003 |
| WO | WO 2007/113285 | * 10/2007 |

OTHER PUBLICATIONS

Serbina et al. Annu. Rev Immunol. 2008. 26:421-52.*
Dawson et al. 2003. Expert Opin Ther. Targets 7:35-48.*
Loetscher et al. J Leukocyte Biology 69:881-884.*
Bowie et al, 1990, Science 247:1306-1310.*
Ngo et al., 1994, The Protein Folding Problem and Tertiary Structure Prediction, Merz et al., eds, Birkhauser, Boston, pp. 433-506.*
Wells, 1990, Biochemistry 29:8509-8517.*
Wang et al. 2001. J. Biol Chem. 276:49213-49220.*
Hemmerich, S. et al. "Identification of residues in the monocyte chemotactic protein-1 that contact the MCP-1 receptor, CCR2" *Biochemistry*, Oct. 5, 1999, pp. 13013-13025, vol. 38, No. 40.
Kim, K-S. et al. "Structural characterization of a monomeric chemokine: Monocyte chemoattractant protein-3" *FEBS Letters*, 1996, pp. 277-282, vol. 395, Nos. 2-3.
Paavola, C.D. et al. "Monomeric monocyte chemoattractant protein-1 (MCP-1) binds and activates the MCP-1 receptor CCR2B" *Journal of Biological Chemistry*, Dec. 11, 1998, pp. 33157-33165, vol. 273, No. 50.
Proudfoot, A.E.I, et al. "Glycosaminoglycan binding and oligomerization are essential for the in vivo activity of certain chemokines" *PNAS*, Feb. 18, 2003, pp. 1885-1890, vol. 100, No. 4.
Jarnagin, K. et al. "Identification of surface residues of the monocyte chemotactic protein 1 that affect signalng through the receptor CCR2" *Biochemistry*, 1999, pp. 16167-16177, vol. 38, No. 49.
Lau, E.K. et al. "Identification of the glycosaminoglycan binding site of the CC chemokine, MCP-1" *Journal of Biological Chemistry*, May 21, 2004, pp. 22294-22305, vol. 279, No. 21.
Brini, E. et al. "Clinical, neuropathological and immunological effects of the administration of a MCP-1 variant on Relapsing-Remitting experimental autoimmune encephalomyelitis mouse model", abstract and poster to be presented at the 23$^{rd}$ Congress of the European Committee for Treatment and Research of Multiple Sclerosis (ECTRIMS) conference, Prague, Czech Republic, Oct. 11-14, 2007.
Johnson, Z. "The Role of Glycosaminoglycan Binding and Oligomerisation in Chemokine Function in Vivo", thesis catalogued on Jul. 13, 2004 in the Senate House Library, University of London, pp. 1-273.

* cited by examiner

*Primary Examiner*—Gary B Nickol
*Assistant Examiner*—Shulamith H Shafer
(74) *Attorney, Agent, or Firm*—Saliwanchik, Lloyd & Saliwanchik

(57) ABSTRACT

Variants of homodimer-forming chemokines, such as human CCL2, having a single amino acid substitution in the dimerization interface that alters the pattern of hydrogen bonds and acting as an obligate monomer, can antagonize natural chemokines and have anti-inflammatory activity in vivo. These variants can be used as active ingredient in pharmaceutical compositions for the treatment of inflammatory, autoimmune, or infectious diseases.

12 Claims, 7 Drawing Sheets

Figure 1

Figure 2:
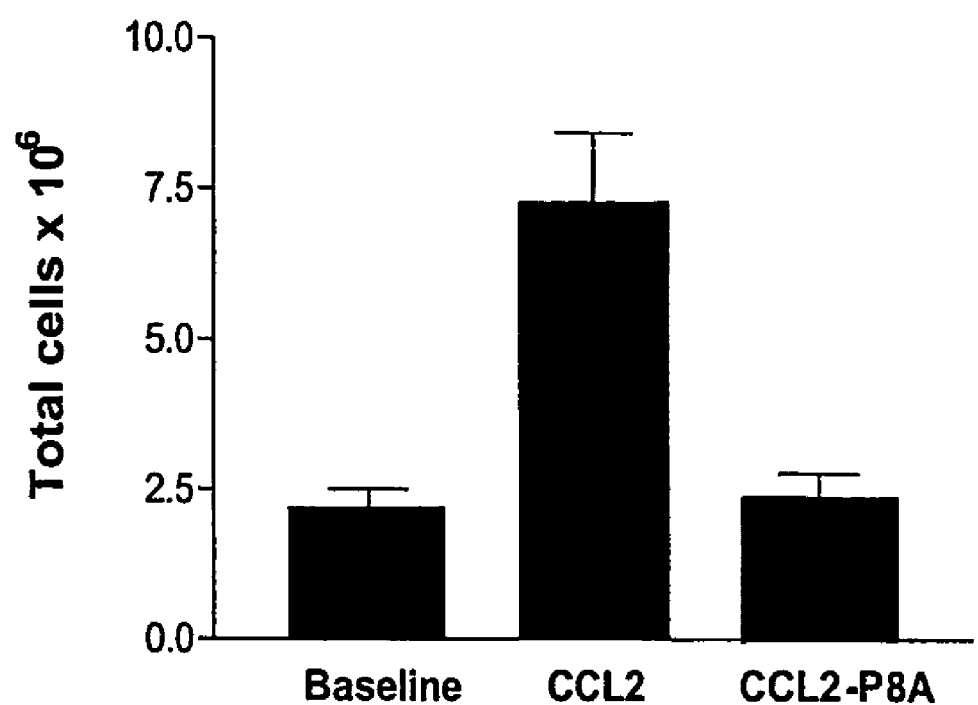

```
CCL2        1 QPDAINAPVT CCYNFTNRKI SVQRLASYRR ITSSKCPKEA VIFKTIVAKE 50
CCL2-P8A    1 QPDAINAAVT CCYNFTNRKI SVQRLASYRR ITSSKCPKEA VIFKTIVAKE 50
CCL2*       1 QPDAINAPVT CCYNFTNRKI SVQRLASYRR ITSSKCPKEA VIFKTIVAKE 50
CCL2*-P8A   1 QPDAINAAVT CCYNFTNRKI SVQRLASYRR ITSSKCPKEA VIFKTIVAKE 50

CCL2        51 ICADPKQKWV QDSMDHLDKQ TQTPKT 76
CCL2-P8A    51 ICADPKQKWV QDSMDHLDKQ TQTPKT 76
CCL2*       51 ICADPKQKWV QDSIDHLDKQ TQTPKT 76
CCL2*-P8A   51 ICADPKQKWV QDSIDHLDKQ TQTPKT 76
```

Figure 3
A)
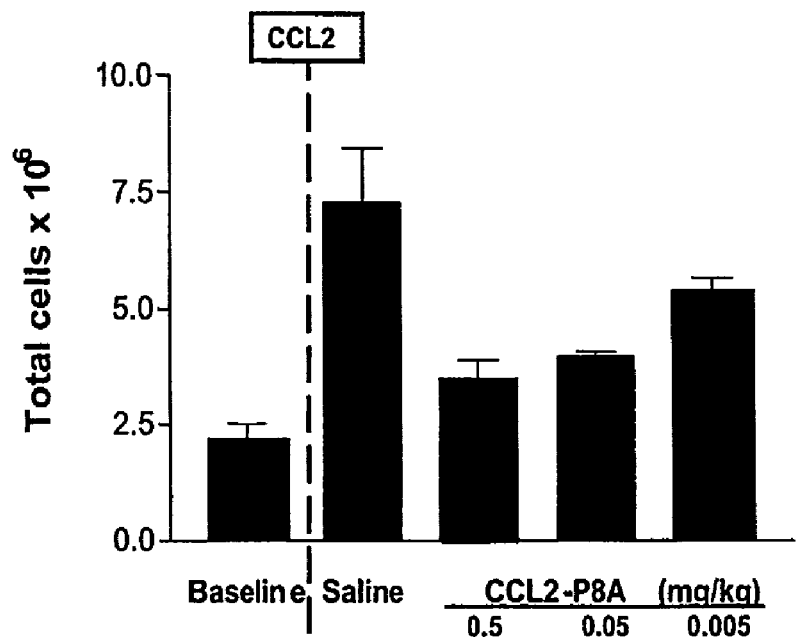
B)
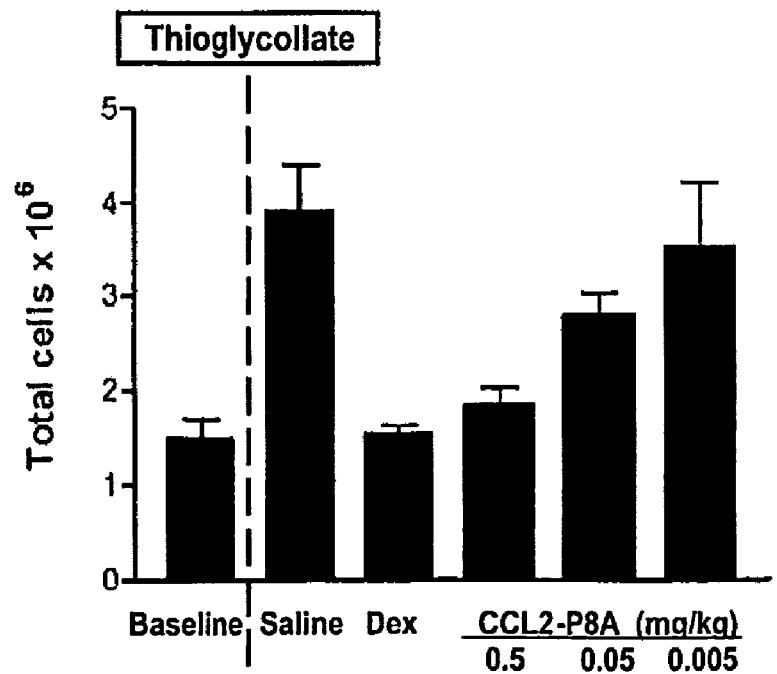

Figure 5
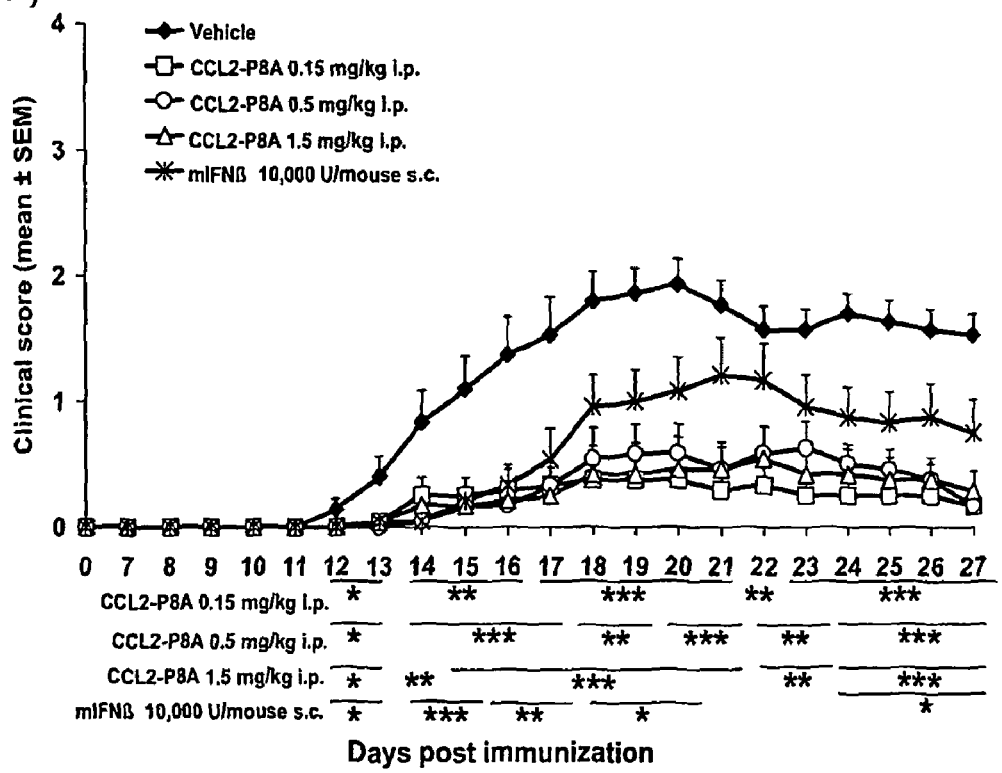
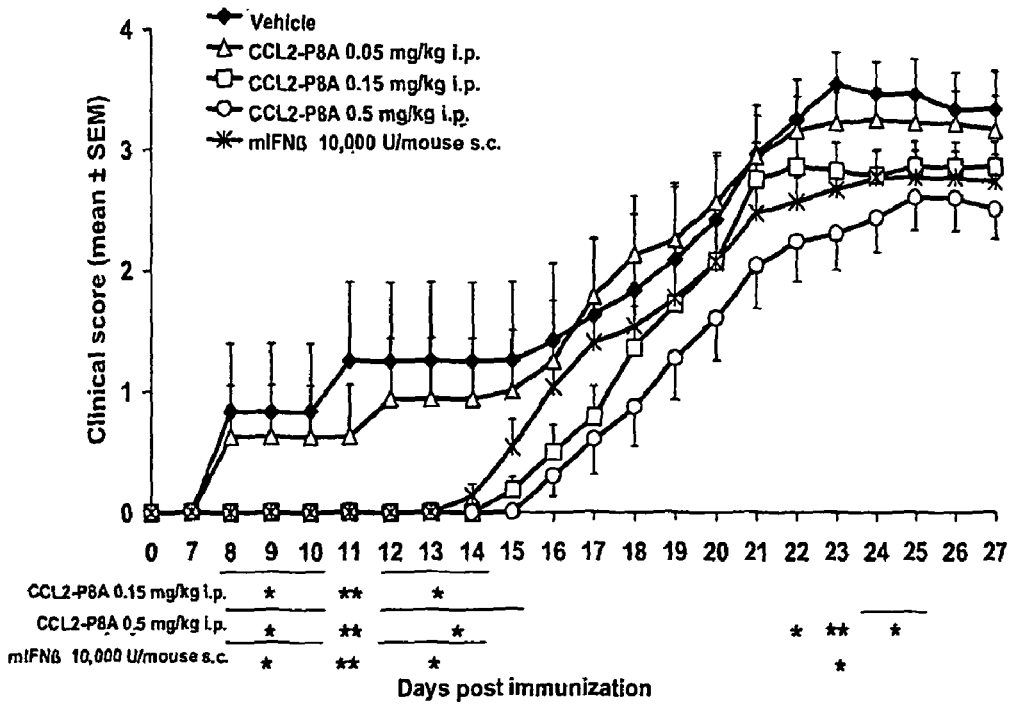

Figure 7

(A)

```
              A A         C       C C
              ↓ ↓         ↓       ↓ ↓
CCL2-P8A   1  QPDAINAAVT  CCYNFTNRKI  SVQRLASYRR  ITSSKCPKEA  VIFKTIVAKE  50

C
                                          ↓
CCL2-P8A  51  ICADPKQKWV  QDSMDHLDKQ  TQTPKT  76
```

(B)

```
  1  MKVSAALLCL  LLIAATFIPQ  GLAQPDAINA  AVTCCYNFTN  RKISVQRLAS   50
 51  YRRITSSKCP  KEAVIFKTIV  AKEICADPKQ  KWVQDSMDHL  DKQTQTPKT E  100
101  PKSCDKTHTC  PPCPAPELLG  GPSVFLFPPK  PKDTLMISRT  PEVTCVVVDV  150
151  SHEDPEVKFN  WYVDGVEVHN  AKTKPREEQY  NSTYRVVSVL  TVLHQDWLNG  200
201  KEYKCKVSNK  ALPAPIEKTI  SKAKGQPREP  QVYTLPPSRE  EMTKNQVSLT  250
251  CLVKGFYPSD  IAVEWESNGQ  PENNYKTTPP  VLDSDGSFFL  YSKLTVDKSR  300
301  WQQGNVFSCS  VMHEALHNHY  TQKSLSLSPG  K
```

THERAPEUTIC USES OF CHEMOKINE VARIANTS

CROSS-REFERENCE TO RELATED APPLICATION

This application is the U.S. national stage application of International Patent Application No. PCT/EP2004/052572, filed Oct. 18, 2004, the disclosure of which is hereby incorporated by reference in its entirety, including all figures, tables and amino acid or nucleic acid sequences.

FIELD OF THE INVENTION

The invention relates to novel therapeutic uses of chemokine variants, and in particular of human CCL2 variants.

BACKGROUND OF THE INVENTION

Chemokines are small, secreted pro-inflammatory proteins, which mediate directional migration of leukocytes from the blood to the site of injury. Depending on the position of the conserved cysteines characterizing this family of proteins, the chemokine family can be divided structurally in C, C—C, C—X—C and C—$X_3$—C chemokines which bind to a series of membrane receptors (Baggiolini M et al., 1997; Fernandez E J and Lolis E, 2002).

These membrane receptors, all heptahelical G-protein coupled receptors, allow chemokines to exert their biological activity on the target cells, which may present specific combinations of receptors according to their state and/or type. The physiological effects of chemokines result from a complex and integrated system of concurrent interactions: the receptors often have overlapping ligand specificity, so that a single receptor can bind different chemokines, as well a single chemokine can bind to different receptors.

Usually chemokines are produced at the site of injury and cause leukocyte migration and activation, playing a fundamental role in inflammatory, immune, homeostatic, hematopoietic, and angiogenic processes. Even though there are potential drawbacks in using chemokines as therapeutic agents (tendency to aggregate and promiscuous binding, in particular), these molecules are considered good target candidates for therapeutic intervention in diseases associated to such processes, by inhibiting specific chemokines and their receptors at the scope to preventing the excessive recruitment and activation of leukocytes (Baggiolini M, 2001; Loetscher P and Clark-Lewis I, 2001; Godessart N and Kunkel S L, 2001).

Studies on structure-activity relationships indicate that chemokines have two main sites of interaction with their receptors, the flexible amino-terminal region and the conformationally rigid loop that follows the second cysteine. Chemokines are thought to dock onto receptors by means of the loop region, and this contact is believed to facilitate the binding of the amino-terminal region that results in receptor activation. This importance of the amino-terminal region has been also demonstrated by testing natural and synthetic chemokines in which this domain is modified or shortened. This processing, following proteolytic digestion, mutagenesis, or chemical modification of amino acids, can either activate or render these molecules inactive, generating compounds with agonistic and/or antagonistic activity. Thus, chemokines with specific modifications in the amino-terminal region have therapeutic potential for inflammatory and autoimmune diseases (Schwarz and Wells, 1999).

CCL2, also known as Monocyte Chemoattractant Protein 1 (MCP-1) or Monocyte Chemotactic And Activating Factor (MCAF), has been identified as having a central role in inflammation, being capable of promoting the recruitment of monocytes and lymphocytes in response to injury and infection signals in various inflammatory diseases, different types of tumors, cardiac allograft, AIDS, and tuberculosis (Yoshimura T et al., 1989; Gu L et al., 1999). The physiological activities associated with CCL2 have been extensively studied by means of transgenic animals, which allowed the demonstration that this chemokine controls not only monocyte recruitment in inflammatory models, but also the expression of cytokines relate d to T helper responses and the initiation of atherosclerosis (Gu L et al., 2000; Gosling J et al, 1999; Lu B et al, 1998).

Structurally, CCL2 consists of a N-terminal loop and a beta sheet overlaid by an alpha helix at the C-terminal end, and forms homodimers, even though has been detected as a monomer in specific experimental conditions (Handel T et al., 1996; Kim K S et al., 1996; Lubkowski J, et al., 1997). As for many other chemokines, the literature provides many examples of structure-activity studies in which CCL2 mutants have been generated by expressing N-terminal truncated or single site substituted variants to assess the role of the deleted or substituted amino acids in CCL2-associated binding activities and other properties (Gong J and Clark-Lewis I, 1995; Zhang Y et al., 1996; Steitz S A et al., 1998; Gu L et al., 1999; Hemmerich S et al., 1999; Seet B T et al., 2001).

In particular, the role of dimerization in CCL2 receptor binding and activation was studied showing that different mutations in the terminal region hindering dimerization may alter some CCL2 activities such as receptor binding affinity, stimulation of chemotaxis, inhibition of adenylate cyclase, and stimulation of calcium influx (Paavola C et al, 1998). While one mutant described by Paavola, herein called P8A*, does not dimerize, but maintains original potency and efficacy, another obligate monomeric mutant described by Paavola, herein called Y13A*, was shown to have a 100-fold weaker binding affinity in vitro, to be a much less potent inhibitor of adenylate cyclase and stimulator of calcium influx in vitro, and unable to stimulate chemotaxis in cell culture. Similarly to Y13A*, a mutant, [1+9-76]MCP-1 (a CCL2 variant lacking residues 2-8), antagonizes CCL2 activities in vitro.

The binding properties of the CCL2 mutant containing the P8A substitution were also studied in an experimental model based upon the recognition of the viral chemokine binding protein M3, demonstrating the efficient binding of this viral protein to this CCL2 mutant (Alexander J M et al., 2002). Moreover it has been shown that monomeric variants of chemokines, such as CCL2-P8A, are devoid of activity in vivo, although fully active and indistinguishable from the dimeric form in vitro (Proudfoot A et al., 2003).

Examples of CCL2 mutants involving residues not affecting the dimerization profile of the resulting protein have been already described in the literature as leading to molecules having antagonistic properties towards CCL2 (U.S. Pat. No. 5,739,103, WO 03/84993). However, there is not indication in the prior art that a specific chemokine mutant, and in particular a CCL2 mutant, being an obligate monomer due to a single site substitution (for example, involving a Proline), may act as a chemokine antagonist.

SUMMARY OF THE INVENTION

It has been surprisingly found that variants of homodimer-forming chemokines, such as CCL2, having a single amino acid substitution in the dimerization interface that alters the pattern of hydrogen bonds, so as to result in an obligate monomer that binds to the receptor and has agonistic properties in vitro, can antagonize natural chemokines and have anti-inflammatory activity in vivo.

The variants described herein are useful as a medicament. Polypeptides comprising SEQ ID NO: 2 and those comprising SEQ ID NO: 2 with a further mutation to isoleucine at position 64 of SEQ ID NO: 2 (SEQ ID NO: 4) are useful as medicaments.

The variants described herein are useful as medicaments for the treatment of autoimmune, inflammatory or infectious diseases. Polypeptides comprising SEQ ID NO: 2 and those comprising SEQ ID NO: 2 with a further mutation to isoleucine at position 64 of SEQ ID NO: 2 (SEQ ID NO: 4) are useful as medicaments for the treatment of autoimmune, inflammatory and infectious diseases. In one example, polypeptides comprising SEQ ID NO: 2 and those comprising SEQ ID NO: 2 with a further mutation to isoleucine at position 64 of SEQ ID NO:2 (SEQ ID NO:4) are useful as medicaments for the treatment of multiple sclerosis.

The variants described herein are further useful in methods for treatment of autoimmune, inflammatory and infectious diseases. Such methods comprise the administration of an effective amount of a monomeric variant of the invention, wherein said variant results from at least an amino acid substitution that alters the pattern of hydrogen bonds at the dimerization interface of said chemokine. Examples of such monomeric variants that can be used in such methods are: a) a polypeptide comprising SEQ ID NO: 2; b) a polypeptide comprising SEQ ID NO: 4; c) an active mutant of a) or b); d) a polypeptide comprising a), b) or c) and an amino acid sequence belonging to a protein other than said chemokine; as well as the corresponding molecules in the form of their active fractions, precursors, salts, derivatives, complexes or conjugates.

The invention further includes pharmaceutical compositions containing a polypeptide comprising the obligate monomeric antagonistic chemokine variants of the Invention.

The Invention further includes fusion proteins comprising an obligate monomeric antagonistic chemokine variant described herein fused to a non-chemokine protein sequence, for example the amino acid sequence of SEQ ID NO: 2 fused to the constant region of a human immunoglobulin heavy chain (SEQ IN NO: 5). The Invention further includes methods for producing these fusion proteins.

The Invention further includes methods for screening for obligate monomeric antagonist chemokine variants described herein comprising:

a) making single point mutations in CCL2 that block its ability to dimerize;
b) identifying said variants that bind to the receptor and show agonistic properties in vitro;
c) identifying said variants from the group identified in (b) above that are further characterized as inhibiting peritoneal cell recruitment.

Other features and advantages of the invention will be apparent from the following detailed description.

DESCRIPTION OF THE FIGURES

FIG. 1: amino acid sequences of human mature CCL2 (residues 24-99 of SWISSPROT Acc. N° P13500; SEQ ID NO: 1), mature CCL2-P8A (SEQ ID NO: 2), mature CCL2* (SEQ ID NO: 3), mature CCL2*-P8A (SEQ ID NO: 4). The mutation in position 64 to Isoleucin (M64I) is boxed in CCL2* and CCL2*-P8A; the relevant mutation P8A is bold and underlined.

FIG. 2: graph comparing the cell recruiting activity of recombinant human CCL2 and CCL2-P8A with the baseline in the peritoneal cell recruiting assay.

FIG. 3: graph showing the dose-response inhibiting activity of CCL2-P8A in peritoneal cell recruitment assays using two different inducers: CCL2 (A) or Thioglycollate (B); the results are compared with the baseline level, a negative control (vehicle only, saline) and a positive control, Dexamethasone (Dex; only in B).

FIG. 4: graph showing the inhibiting activity of CCL2-P8A in ovalbumin-induced lung inflammation assay; the result is compared with the baseline level, and a negative control (saline).

FIG. 5: Graph showing the efficacy of CCL2-P8A in reducing clinical scores in an animal model for multiple sclerosis called EAE (Experimental Autoimmune Encephalomyelitis), either when the animals present a mild disease with low clinical score (not more than 2; A) or a severe disease with high clinical score (at least 3; B); the data are compared to those observed using the vehicle only (negative control) or positive control for the EAE model (mouse Interferon beta); the number of asterisks on the bottom of each graph indicate the level of statistical significance of the effect observed when compared to the negative control at each time point (* means $p<0.05$,  means $p<0.01$, and * means $p<0.001$, as calculated by one-way ANOVA followed by Fisher test).

FIG. 6: graph showing the inhibiting activity of CCL2-P8A when administered at different dosages in an animal model for skin inflammation (DNFB-induced inflammation on the ear of sensitized mice); the effect of CCL2-P8A on the volume of the ear swelling volume after the treatment, and it is compared with the following controls: animals not sensitized but challenged at day 5 with DNFB (A), animal sensitized and challenged with DNFB but only vehicle treated (B), and animals treated with Dexamethasone (Dex; administered in the same manner of CCL2-P8A). The values were measured at day 6 (the day after the treatment and the challenge).

FIG. 7: Alternative forms of CCL2-P8A that can be generated by single/multiple amino acid addition and/or substitution (A) or by fusion to residues 243-474 of human immunoglobulin lambda heavy chain IgG1 (B; CCL2 signal sequence is double underlined, mature CCL2-P8A is underlined) (SEQ ID NO:5).

DETAILED DESCRIPTION OF THE INVENTION

In view of the above mentioned evidences in the prior art, there is no indication that a CCL2 variant, resulting from at least single amino acid substitution in the dimerization interface that alters the pattern of hydrogen bonds so as to result in an obligate monomer binding to the receptor and having agonistic properties in vitro, can antagonize CCL2 in vivo, and in general can inhibit cell recruitment and/or inflammatory reactions.

The single amino acid substitution is preferably at position 8 in human mature CCL2, and in particular it consists of replacing Proline in position 8 with an Alanine. These variants do not contain an additional mutation in the position corresponding to 9, 10, or 13 of human mature CCL2.

An example of the above described substitutions is monomeric variant of the mature form of CCL2 called CCL2-P8A which can be expressed either as including the single substitution of the Proline in position 8 to Alanine (SEQ ID NO: 2) or as including a further substitution (improving expression of the protein) of Methionine 64 to Isoleucine (SEQ ID NO: 4). The substitution of Proline 8 to Alanine (an amino acid having a different orientation of the chemical group possibly forming hydrogen bonds) generate a CCL2 variant acting as an obligate monomer. CCL2-P8A and CCL2*-P8A can be considered as molecule having equivalent activity.

Pharmaceutical uses, methods, and compositions that can be consequently envisaged for these specific obligate monomeric variants of CCL2, called CCL2-P8A and CCL2*-P8A, can be also envisaged for any other obligate monomeric variant of CCL2, or of other chemokines that are naturally active as dimers, that are generated in the same manner. These mutants should present antagonistic and inhibitory properties similar to those of CCL2-P8A and CCL2*-P8A against the natural chemokine, and therefore they should have a medical applicability.

One aspect of the present invention is the use of an obligate monomeric variant of a homodimer-forming chemokine, for example CCL2 which is known to be a therapeutic target for various diseases, such as autoimmune, inflammatory, or infectious diseases. Such variants result from at least an amino acid substitution that alters the pattern of hydrogen bonds at the dimerization interface of said chemokine, so as to result in an obligate monomer that binds to the receptor and has agonostic properties in vitro and antagonistic properties in vivo, as active ingredient in a pharmaceutical composition, in particular for the treatment or prevention of autoimmune, inflammatory, or infectious diseases. These in vivo antagonistic properties may become evident in assays allowing the evaluation of properties such as the effect cell recruitment in the peritoneum following the induction with an inflammatory molecule (a chemokine such CCL2 itself, thioglycollate, or ovalbumin).

The obligate monomeric variant may result from a single amino acid substitution in the dimerization interface that alters the pattern of hydrogen bonds. More preferably, being proline an amino acid well known to be particularly relevant for establishing stereospecific hydrogen bonds involved in the formation of protein complexes such as homodimers, the single amino acid substitution should be the substitution of a proline with non-proline amino acid. Alternatively, the single amino acid substitution should be the substitution of non-proline amino acid with a proline, so that the stereospecificity of hydrogen bonds results altered.

Alternative forms of the monomeric variants of the homodimer-forming chemokines above defined that can be used as active ingredients in pharmaceutical compositions include:

a) an active mutant; or b) a polypeptide comprising said variant, or said active mutant, and an amino acid sequence belonging to a protein sequence other than to said chemokine.

The term "active" means that such alternative compounds should maintain the functional features of the CCL2 mutants of the present invention, i.e. should antagonize CCL2 in vivo and inhibit cell recruitment and/or inflammatory reactions.

An obligate monomeric chemokine antagonist as defined herein, as an active compound according to the Invention, can be in the form of their active fractions, precursors, salts, derivatives, complexes or conjugates.

These alternative compounds are intended to comprehend molecules with changes to the sequence of the monomeric variants of the homodimer-forming chemokines that do not affect the basic characteristics disclosed herein. For example, CCL2*-P8A has been generated on the basis of a mutant of CCL2 (CCL2-M64I or CCL2*) that maintains normal CCL2 activities but has improved properties regarding the recombinant expression.

The antagonistic properties of the monomeric variants of homodimer-forming chemokines defined above, and exemplified herein using CCL2-P8A as CCL2 antagonist, can be maintained, or even potentiated, in the active mutants. This category of molecules includes natural or synthetic analogs of said sequence, wherein one or more amino acid residues have been added, deleted, or substituted, provided they display the same biological activity characterized in the present invention at comparable or higher levels, as determined by means known in the art and disclosed in the Examples below.

Natural analogs are intended to be the corresponding sequences of human chemokines proteins identified in other organisms, like mouse CCL2 (SWISSPROT Acc. No P10148). Artificial analogs of the monomeric variants of homodimer-forming chemokines are intended to be polypeptides prepared by known chemical synthesis and/or by site-directed mutagenesis techniques, combinatorial technologies at the level of encoding DNA sequence (such as DNA shuffling, phage display/selection), by computer-aided design studies, or by any other known technique suitable thereof, which provide a finite set of substantially corresponding mutated or shortened peptides or polypeptides which can be routinely obtained and tested by one of ordinary skill in the art using the teachings presented in the prior art and in the Examples below.

For example, specific artificial mutants may have one or more amino acids being substituted in other positions of CCL2 and found relevant for generating CCL2 antagonists (WO 03/84993).

In accordance with the present invention, preferred changes in the active mutants are commonly known as "conservative" or "safe" substitutions, and involve non-basic residues. Conservative amino acid substitutions are those with amino acids having sufficiently similar chemical properties, in order to preserve the structure and the biological function of the molecule. It is clear that insertions and deletions of amino acids may also be made in the above defined sequences without altering their function, particularly if the insertions or deletions only involve a few amino acids, e.g., under ten, and preferably under three, and do not remove or displace amino acids which are critical to the functional conformation of a protein or a peptide.

The literature provide many models on which the selection of conservative amino acids substitutions can be performed on the basis of statistical and physico-chemical studies on the sequence and/or the structure of natural protein (Rogov S I and Nekrasov A N, 2001). Protein design experiments have shown that the use of specific subsets of amino acids can produce foldable and active proteins, helping in the classification of amino acid "synonymous" substitutions which can be more easily accommodated in protein structure, and which can be used to detect functional and structural homologs and paralogs (Murphy L R et al., 2000). The synonymous amino acid groups and more preferred synonymous groups are those defined in Table I. For example, the substitution of Methionine 64 with Isoleucine common to CCL2* and CCL2*-P8A have been chosen using a similar criteria.

A further group of active mutants of the monomeric variants of the homodimer-forming chemokines defined above are peptide mimetics (also called peptidomimetics), in which the nature of peptide or polypeptide has been chemically modified at the level of amino acid side chains, of amino acid chirality, and/or of the peptide backbone. These alterations are intended to provide monomeric variants of the homodimer-forming chemokines having similar or improved properties in terms of preparation, potency and/or pharmacokinetics features.

For example, when the peptide is susceptible to cleavage by peptidases following injection into the subject is a problem, replacement of a particularly sensitive peptide bond with a non-cleavable peptide mimetic can provide a peptide more stable and thus more useful as a therapeutic. Similarly, the replacement of an L-amino acid residue is a standard way of rendering the peptide less sensitive to proteolysis, and finally more similar to organic compounds other than peptides. Also useful are amino-terminal blocking groups such as t-butyloxycarbonyl, acetyl, theyl, succinyl, methoxysuccinyl, suberyl, adipyl, azelayl, dansyl, benzyloxycarbonyl, fluorenyl methoxycarbonyl, methoxyazelayl, methoxyadipyl, methoxysuberyl, and 2,4-dinitrophenyl. Many other modifications providing increased potency, prolonged activity, easiness of purification, and/or increased half-life are known in the art (WO 02/10195; Villain M et al., 2001).

Preferred alternative, "synonymous" groups for amino acids included in peptide mimetics are those defined in Table II. A non-exhaustive list of amino acid derivatives also include aminoisobutyric acid (Aib), hydroxyproline (Hyp), 1,2,3,4-tetrahydro-isoquinoline-3-COOH, indoline-2carboxylic acid, 4-difluoro-proline, L-thiazolidine-4-carboxylic acid, L-homoproline, 3,4-dehydro-proline, 3,4-dihydroxyphenylalanine, cyclohexyl-glycine, and phenylglycine.

By "amino acid derivative" is intended an amino acid or amino acid-like chemical entity other than one of the 20 genetically encoded naturally occurring amino acids. In particular, the amino acid derivative may contain substituted or non-substituted alkyl moieties that can be linear, branched, or cyclic, and may include one or more heteroatoms. The amino acid derivatives can be made de novo or obtained from commercial sources (Calbiochem-Novabiochem AG, Switzerland; Bachem, USA).

The techniques for the synthesis and the development of peptide mimetics, as well as non-peptide mimetics, are well known in the art (Hruby V J and Balse P M, 2000; Golebiowski A et al., 2001). Various methodology for incorporating unnatural amino acids into proteins, using both in vitro and in vivo translation systems, to probe and/or improve protein structure and function are also disclosed in the literature (Dougherty D A, 2000).

The present Invention discloses the use of monomeric variants of the homodimer-forming chemokines, and their active mutants, as active ingredients in pharmaceutical compositions, as well as of proteins comprising their amino acid sequence and an amino acid sequence belonging to a protein sequence other than said chemokine. This heterologous latter sequence should provide additional properties without impairing the pharmaceutical applicability. Examples of such additional properties are an easier purification procedure, a longer lasting half-life in body fluids, or extracellular localization. This latter feature is of particular importance for defining a specific group of fusion or chimeric proteins included in the above definition since it allows these monomeric variants to be localized in the space where not only where the isolation and purification of these peptides is facilitated, but also where CCL2 naturally interacts with other molecules.

Design of the moieties, ligands, and linkers, as well methods and strategies for the construction, purification, detection and use of fusion proteins are widely discussed in the literature (Nilsson J et al., 1997; "Applications of chimeric genes and hybrid proteins" Methods Enzymol. Vol. 326-328, Academic Press, 2000; WO 01/77137). Additional protein sequences which can be used to generate alternative forms of these obligate monomeric variants of homodimer-forming chemokines as defined above are the ones of extracellular domains of membrane-bound protein, immunoglobulin constant region (Fc region), multimerization domains, extracellular proteins, signal peptide-containing proteins, export signal-containing proteins. The choice of one or more of these sequences to be fused to the monomeric variant is functional to specific use of said agent. When the additional protein sequence, as in the case of the sequence of extracellular, export signal, or signal-peptide containing proteins, allows the monomeric variant to be secreted in the extracellular space, the agent can be more easily collected and purified from cultured cells in view of further processing or, alternatively, the cells can be directly used or administered.

The obligate monomeric variants of homodimer-forming chemokines defined above can be also used in other preferred forms, for example as active fractions, precursors, salts, derivatives, conjugates or complexes.

The term "fraction" refers to any fragment of the polypeptidic chain of the compound itself, alone or in combination with related molecules or residues bound to it, for example residues of sugars or phosphates, or aggregates of the original polypeptide or peptide. Such molecules can result also from other modifications which do not normally alter primary sequence, for example in vivo or in vitro chemical derivativization of peptides (acetylation or carboxylation), those made by modifying the pattern of phosphorylation (introduction of phosphotyrosine, phosphoserine, or phosphothreonine residues) or glycosylation (by exposing the peptide to enzymes which affect glycosylation e.g., mammalian glycosylating or deglycosylating enzymes) of a peptide during its synthesis and processing or in further processing steps.

The "precursors" are compounds which can be converted into the compounds of present invention by metabolic and enzymatic processing prior or after the administration to the cells or to the body.

The term "salts" herein refers to both salts of carboxyl groups and to acid addition salts of amino groups of the peptides, polypeptides, or analogs thereof, of the present invention. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids such as, for example, hydrochloric acid or sulfuric acid, and salts with organic acids such as, for example, acetic acid or oxalic acid. Any of such salts should have substantially similar activity to the peptides and polypeptides of the invention or their analogs.

The term "derivatives" as herein used refers to derivatives which can be prepared from the functional groups present on the lateral chains of the amino acid moieties or on the N- or C-terminal groups according to known methods. Such derivatives include for example esters or aliphatic amides of the carboxyl-groups and N-acyl derivatives of free amino groups or O-acyl derivatives of free hydroxyl-groups and are formed with acyl-groups as for example alcanoyl- or aroyl-groups.

Useful conjugates or complexes of obligate monomeric variants of homodimer-forming chemokines defined above can be generated, using molecules and methods known in the art of the interaction with receptor or other proteins (radioactive or fluorescent labels, biotin), therapeutic efficacy (cytotoxic agents), or improving the agents in terms of drug delivery efficacy, such as polyethylene glycol and other natural or synthetic polymers (Harris J M and Chess R B, 2003; Greenwald R B et al., 2003; Pillai O and Panchagnula R, 2001). Residues can be used for attachment, provided they have a side-chain amenable for polymer attachment (i.e., the side chain of an amino acid bearing a functional group, e.g., lysine, aspartic acid, glutamic acid, cysteine, histidine, etc.). Alternatively, a residue at these sites can be replaced with a different amino acid having a side chain amenable for polymer attachment. Also, the side chains of the genetically encoded amino acids can be chemically modified for polymer attachment, or unnatural amino acids with appropriate side chain functional groups can be employed. Polymer attachment may be not only to the side chain of the amino acid naturally occurring in a specific position of the antagonist or to the side chain of a natural or unnatural amino acid that replaces the amino acid naturally occurring in a specific position of the antagonist, but also to a carbohydrate or other moiety that is attached to the side chain of the amino acid at the target position.

Polymers suitable for these purposes are biocompatible, namely, they are non-toxic to biological systems, and many such polymers are known. Such polymers may be hydrophobic or hydrophilic in nature, biodegradable, non-biodegradable, or a combination thereof. These polymers include natural polymers (such as collagen, gelatin, cellulose, hyaluronic acid), as well as synthetic polymers (such as polyesters, poly-orthoesters, polyanhydrides). Examples of hydrophobic non-degradable polymers include polydimethyl siloxanes, polyurethanes, polytetrafluoroethylenes, polyethylenes, polyvinyl chlorides, and polymethyl methaerylates. Examples of hydrophilic non-degradable polymers include poly(2-hydroxyethyl methacrylate), polyvinyl alcohol, poly (N-vinyl pyrrolidone), polyalkylenes, polyacrylamide, and copolymers thereof. Preferred polymers comprise as a sequential repeat unit ethylene oxide, such as polyethylene glycol (PEG).

The preferred method of attachment employs a combination of peptide synthesis and chemical ligation. Advantageously, the attachment of a water-soluble polymer will be through a biodegradable linker, especially at the amino-terminal region of a protein. Such modification acts to provide the protein in a precursor (or "pro-drug") form, that, upon degradation of the linker releases the protein without polymer modification.

As a general procedure, the obligate monomeric variants of homodimer-forming chemokines defined above can be produced may be prepared by any procedure known in the art, including recombinant DNA-related technologies and chemical synthesis technologies.

Many books and reviews provides teachings on how to clone and produce recombinant proteins using vectors and prokaryotic (e.g. *E. coli*) or eukaryotic host cells, such as some titles in the series "A Practical Approach" published by Oxford University Press ("DNA Cloning 2: Expression Systems", 1995; "DNA Cloning 4: Mammalian Systems", 1996; "Protein Expression", 1999; "Protein Purification Techniques", 2001).

Another embodiment according to the Invention is the nucleic acid sequence encoding for the obligate monomeric chemokine variant antagonist described herein.

The DNA sequence coding for the obligate monomeric variants of homodimer-forming chemokines can be inserted and ligated into a suitable episomal or non-homologously integrating vectors, which can be introduced in the appropriate host cells by any suitable means (transformation, transfection, conjugation, protoplast fusion, electroporation, calcium phosphate-precipitation, direct microinjection, etc.) to transform them. Factors of importance in selecting a particular plasmid or viral vector include: the ease with which recipient cells that contain the vector, may be recognized and selected from those recipient cells which do not contain the vector; the number of copies of the vector which are desired in a particular host; and whether it is desirable to be able to "shuttle" the vector between host cells of different species.

The vectors should allow the expression of the isolated or fusion protein including the antagonist of the invention in the prokaryotic or eukaryotic host cell under the control of transcriptional initiation/termination regulatory sequences, which are chosen to be constitutively active or inducible in said cell. A cell line substantially enriched in such cells can be then isolated to provide a stable cell line.

For eukaryotic hosts (e.g. yeasts, insect or mammalian cells), different transcriptional and translational regulatory sequences may be employed, depending on the nature of the host. They may be derived form viral sources, such as adenovirus, bovine papilloma virus, Simian virus or the like, where the regulatory signals are associated with a particular gene which has a high level of expression. Examples are the TK promoter of the Herpes virus, the SV40 early promoter, the yeast gal4 gene promoter, etc. Transcriptional initiation regulatory signals may be selected which allow for repression and activation, so that expression of the genes can be modulated. The cells which have been stably transformed by the introduced DNA can be selected by also introducing one or more markers which allow for selection of host cells which contain the expression vector. The marker may also provide for phototrophy to an auxotropic host, biocide resistance, e.g. antibiotics, or heavy metals such as copper, or the like. The selectable marker gene can either be directly linked to the DNA gene sequences to be expressed, or introduced into the same cell by co-transfection. Additional elements may also be needed for optimal synthesis of the proteins.

Host cells may be either prokaryotic or eukaryotic. Preferred are eukaryotic hosts, e.g. mammalian cells, such as human, monkey, mouse, and Chinese Hamster Ovary (CHO) cells, because they provide post-translational modifications to protein molecules, including correct folding or glycosylation at correct sites. Also yeast cells can carry out post-translational peptide modifications including glycosylation. A number of recombinant DNA strategies exist which utilize strong promoter sequences and high copy number of plasmids which can be utilized for production of the desired proteins in yeast. Yeast recognizes leader sequences in cloned mammalian gene products and secretes peptides bearing leader sequences (i.e., pre-peptides).

For long-term, high-yield production of a recombinant polypeptide, stable expression is preferred. For example, cell lines which stably express the polypeptide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells that successfully express the introduced sequences. Resistant clones of stably transformed cells may be proliferated using tissue culture techniques appropriate to the cell type. A cell line substantially enriched in such cells can be then isolated to provide a stable cell line.

Mammalian cell lines available as hosts for expression are known in the art and include many immortalised cell lines available from the American Type Culture Collection (ATCC) including, but not limited to, Chinese hamster ovary (CHO), HeLa, baby hamster kidney (BHK), monkey kidney (COS), C127, 3T3, BHK, HEK 293, Bowes melanoma and human hepatocellular carcinoma (for example Hep G2) cells and a number of other cell lines. In the baculovirus system, the materials for baculovirus/insect cell expression systems are commercially available in kit form from, inter alia, the "MaxBac" kit (Invitrogen).

Examples of chemical synthesis technologies are solid phase synthesis and liquid phase synthesis. As a solid phase synthesis, for example, the amino acid corresponding to the C-terminus of the peptide to be synthetized is bound to a support which is insoluble in organic solvents, and by alternate repetition of reactions, one wherein amino acids with their amino groups and side chain functional groups protected with appropriate protective groups are condensed one by one in order from the C-terminus to the N-terminus, and one where the amino acids bound to the resin or the protective group of the amino groups of the peptides are released, the peptide chain is thus extended in this manner. Solid phase synthesis methods are largely classified by the tBoc method and the Fmoc method, depending on the type of protective group used. Typically used protective groups include tBoc (t-butoxycarbonyl), Cl-Z (2-chlorobenzyloxycarbonyl), Br-Z (2-bromobenzyloxycarbonyl), Bzl (benzyl), Fmoc (9-fluorenylmethoxycarbonyl), Mbh (4,4'-dimethoxydibenzhydryl), Mtr (4-methoxy-2,3,6-trimethylbenzenesulphonyl), Trt (trityl), Tos (tosyl), Z (benzyloxycarbonyl) and Cl2-Bzl (2,6-dichlorobenzyl) for the amino groups; NO2 (nitro) and Pmc (2,2,5,7,8-pentamethylchromane-6-sulphonyl) for the guanidino groups; and tBu (t-butyl) for the hydroxyl groups). After synthesis of the desired peptide, it is subjected to the de-protection reaction and cut out from the solid support. Such peptide cutting reaction may be carried with hydrogen fluoride or tri-fluoromethane sulfonic acid for the Boc method, and with TFA for the Fmoc method. Totally synthetic CCL2 proteins are disclosed in the literature (Brown A et al., 1996).

Purification of synthetic or recombinant monomeric variants of homodimer-forming chemokines defined above can be carried out by any one of the methods known for this purpose, i.e. any conventional procedure involving extraction, precipitation, chromatography, electrophoresis, or the like. A further purification procedure that may be used in preference for purifying the protein of the invention is affinity chromatography using monoclonal antibodies or affinity groups, which bind the target protein and are produced and immobilized on a gel matrix contained within a column. Impure preparations containing the proteins are passed through the column. The protein will be bound to the column by heparin or by the specific antibody while the impurities will pass through. After washing, the protein is eluted from the gel by a change in pH or ionic strength. Alternatively, HPLC (High Performance Liquid Chromatography) can be used. The elution can be carried using a water-acetonitrile-based solvent commonly employed for protein purification.

The monomeric variant of a homodimer-forming chemokine can be used in the pharmaceutical composition for the treatment or prevention of autoimmune, inflammatory, or infectious diseases. In particular, the results provided in the examples regarding an animal model for multiple sclerosis shows that these monomeric variants can be used in the pharmaceutical composition for the treatment or prevention of multiple sclerosis.

Another aspect of the invention is a monomeric variant of a homodimer-forming chemokine, wherein said variant results from at least an amino acid substitution that alters the pattern of hydrogen bonds at the dimerization interface of said chemokine, used as a medicament. Examples of such variants are disclosed herein as CCL2-P8A and CCL2*-P8A. However, the teaching of the Invention allows the identification, production and testing of similar molecules on the basis of the sequence and the activities of other chemokines.

In particular, these monomeric variants can be chosen from:

a) CCL2-P8A (SEQ ID NO: 2);
b) CCL2*-P8A (SEQ ID NO: 4);
c) An active mutant of (a) or (b); or
d) A polypeptide comprising (a), (b), or (c), and an amino acid sequence belonging to a protein sequence other than said chemokine;

as well as the corresponding monomeric variants in the form of their active fractions, precursors, salts, derivatives, complexes or conjugates.

Another aspect of the invention is a pharmaceutical composition containing a monomeric variant of a homodimer-forming chemokine as active ingredient, wherein said variant result from at least an amino acid substitution that alters the pattern of hydrogen bonds at the dimerization interface of said chemokine, such as CCL2-P8A or CCL2*-P8A, optionally in the forms defined above (such as active mutants, polypeptides comprising them, or conjugates) as well as DNA coding or cells expressing them.

The pharmaceutical compositions of the invention may contain suitable pharmaceutically acceptable carriers, biologically compatible vehicles and additives that are suitable for administration to an animal (for example, physiological saline) and eventually comprising auxiliaries (like excipients, stabilizers or diluents) that facilitate the processing of the active compounds into preparations that can be used pharmaceutically. The pharmaceutical compositions may be formulated in any acceptable way to meet the needs of the mode of administration. For example, the use of biomaterials and other polymers for drug delivery, as well the different techniques and models to validate a specific mode of administration are disclosed in literature (Luo B and Prestwich G D, 2001; Cleland J L et al., 2001).

An "effective amount" refers to an amount of the active ingredients that is sufficient to affect the course and the severity of the disease, leading to the reduction or remission of such pathology. The effective amount will depend on the route of administration and the condition of the patient.

"Pharmaceutically acceptable" is meant to encompass any carrier, which does not interfere with the effectiveness of the biological activity of the active ingredient and that is not toxic to the host to which is administered. For example, for parenteral administration, the above active ingredients may be formulated in unit dosage form for injection in vehicles such as saline, dextrose solution, serum albumin and Ringer's solution. Carriers can be selected also from starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the various oils, including those of petroleum, animal, vegetable or synthetic origin (peanut oil, soybean oil, mineral oil, sesame oil).

Any accepted mode of administration can be used and determined by those skilled in the art to establish the desired blood levels of the active ingredients. For example, administration may be by various parenteral routes such as subcutaneous, intravenous, intradermal, intramuscular, intraperitoneal, intranasal, transdermal, oral, or buccal routes. Parenteral administration can be by bolus injection, by gradual perfusion over time or controlled release dosage forms, including depot injections, osmotic pumps, and the like, for the prolonged administration of the polypeptide at a predetermined rate, preferably in unit dosage forms suitable for single administration of precise dosages. Preparations for parenteral administration include sterile aqueous or non-aqueous solutions, suspensions, and emulsions, which may contain auxiliary agents or excipients known in the art, and can be prepared according to routine methods. In addition, suspension of the active compounds as appropriate oily injection suspensions may be administered. Suitable lipophilic solvents or vehicles include fatty oils, for example, sesame oil, or synthetic fatty acid esters, for example, sesame oil, or synthetic fatty acid esters, for example, ethyl oleate or triglycerides. Aqueous injection suspensions that may contain substances increasing the viscosity of the suspension include, for example, sodium carboxymethyl cellulose, sorbitol, and/or dextran. Optionally, the suspension may also contain stabilizers. Pharmaceutical compositions include suitable solutions for administration by injection, and contain from about 0.01 to 99 percent, preferably from about 20 to 75 percent of active compound together with the excipient. Compositions that can be administered rectally include suppositories.

It is understood that the dosage administered will be dependent upon the age, sex, health, and weight of the recipient, kind of concurrent treatment, if any, frequency of treatment, and the nature of the effect desired. The dosage will be tailored to the individual subject, as is understood and determinable by one of skill in the art. The total dose required for each treatment may be administered by multiple doses or in a single dose. The pharmaceutical composition of the present invention may be administered alone or in conjunction with other therapeutics directed to the condition, or directed to other symptoms of the condition. Usually a daily dosage of active ingredient is comprised between 0.01 to 100 milligrams per kilogram of body weight. Ordinarily 1 to 40 milligrams per kilogram per day given in divided doses or in sustained release form is effective to obtain the desired results. Second or subsequent administrations can be performed at a dosage, which is the same, less than, or greater than the initial or previous dose administered to the individual.

Another object of the present invention is a method for treating or preventing autoimmune or inflammatory (such as multiple sclerosis), or infectious diseases comprising the administration of an effective amount of a monomeric variants of homodimer-forming chemokines, wherein said variant result from at least an amino acid substitution that alters the pattern of hydrogen bonds at the dimerization interface of said chemokine. Examples of such monomeric variants that can be used in such methods are:
a) CCL2-P8A (SEQ ID NO: 2);
b) CCL2*-P8A (SEQ ID NO: 4);
c) An active mutant of (a) or (b);
d) A polypeptide comprising (a), (b), or (c), and an amino acid sequence belonging to a protein sequence other than said chemokine;

as well as the corresponding monomeric variants in the form of their active fractions, precursors, salts, derivatives, complexes or conjugates.

A non-limitative list of examples for autoimmune, inflammatory, or infectious diseases mentioned above regarding the uses, the variants, and the methods of the invention are the following: arthritis, rheumatoid arthritis (RA), psoriatic arthritis, osteoarthritis, systemic lupus erythematosus (SLE), systemic sclerosis, scleroderma, polymyositis, glomerulonephritis, fibrosis, fibrosis, allergic or hypersensitivity diseases, dermatitis, asthma, chronic obstructive pulmonary disease (COPD), inflammatory bowel disease (IBD), Crohn's diseases, ulcerative colitis, multiple sclerosis, cancer, septic shock, viral or HIV infections, transplantation, airways inflammation, graft-versus-host disease (GVHD) and atherosclerosis.

The therapeutic applications of the polypeptides of the invention and of the related reagents can be evaluated (in terms or safety, pharmacokinetics and efficacy) by the means of the in vivo or in vitro assays making use of animal cell, tissues and models (Coleman R A et al., 2001; Li A P, 2001; Methods Mol. Biol vol. 138, "Chemokines Protocols", edited by Proudfoot A et al., Humana Press Inc., 2000; Methods Enzymol, vol. 287 and 288, Academic Press, 1997).

Another aspect of the Invention are methods for screening for obligate monomeric antagonist chemokine variants described herein comprising:
a) making single point mutations in CCL2 that block its ability to dimerize;
b) identifying said variants that bind to the receptor and show agonistic properties in vitro;
c) identifying said variants from the group identified in (b) above that are further characterized as inhibiting peritoneal cell recruitment.

This evaluation of these properties can be made using techniques known in the art, and shown in the examples, applying a molecule known to induce inflammation and peritoneal cell recruitment, for example a chemokine such as CCL2 itself, thioglycollate, or ovalbumin.

The present invention has been described with reference to the specific embodiments, but the content of the description comprises all modifications and substitutions, which can be brought by a person skilled in the art without extending beyond the meaning and purpose of the claims.

The invention will now be described by means of the following Examples, which should not be construed as in any way limiting the present invention.

EXAMPLES

Example 1

Cloning, Expression, and Purification of the Recombinant Proteins

Mature CCL2 (FIG. 1; SEQ ID NO: 1) and the CCL2-P8A mutant proteins (FIG. 1; SEQ ID NO: 2), mature CCL2* (FIG. 1; SEQ ID NO: 3) and the CCL2*-P8A mutant proteins (FIG. 1; SEQ ID NO: 4) were generated and expressed as recombinant proteins in E. coli as described in the literature (Paavola C D et al, 1998) on the basis of the sequence of the mature form of human CCL2/MCP-1, corresponding to the segment 24-99 of the precursor molecule. For CCL2* and CCL2*-P8A, the substitution of a Methionine with an Isoleucine in position 64 improves the purity and homogeneity of the mutants by eliminating the formation of species containing methionine-sulfoxide at position 64.

Briefly, the genes for CCL2 for CCL2* was constructed by standard gene synthesis techniques with optimal codon usage for expression in E. coli and a codon for methionine added at the 5' end of the sequence encoding mature human CCL2 or CCL2*. Mutant constructs including Alanine in position 8 were made by polymerase chain reaction mutagenesis of the CCL2 or CCL2* template and cloned into a pET3a vector (Novagen) between the Xho I and Nde I sites.

Plasmids encoding CCL2*-based proteins were used to transform TAP302 cells, which are BL21 pLys S cells engineered with a thioredoxin reductase knockout to make the intracellular redox potential more conducive to disulfide bond formation. Using this strain, disulfide bonds appear to be formed in the cell, eliminating the need for a refolding step.

All constructs were obtained and controlled by standard molecular biology technologies (PCR mutagenesis and amplification, DNA sequencing, restriction digestion). One of the clones containing the correct sequence of MCP-1 (P8A) was subsequently used to produce the protein in *E. coli*. The plasmids were also used to transform BL21 Star™ (DE3) (Invitrogen Cat no C6010-03) or BL21 DE3 (Novagen Cat n° 69387-3).

CCL2, CCL2* and CCL2*-P8A are expressed and purified as described in the original article, using a sonication step, a lysis step and a chromatographic step (SP—Sepharose column; elution with a gradient of NaCl in 10 mM K2PO4, pH 7.5). Peak fractions were pooled and further purified by reversed-phase HPLC (C18 column with a 5-μm particle size and 300-Å pore size). Proteins were eluted using a gradient of increasing acetonitrile containing 0.1% trifluoroacetic acid; typically, proteins eluted at 34±5% acetonitrile. They were then lyophilized, dissolved at 1 mg/ml in 35 mM Tris, pH 8, reacted with 15 μg of aminopeptidase (Peprotech, Rock Hill, N.J.)/1 mg of protein for 36 h at room temperature, and repurified by reversed-phase HPLC. Aminopeptidase treatment removes only the N-terminal methionine, generating either a N-terminal Glutamin or N-terminal pyro-Glutamic acid (there is no effect on biological activity due to this difference), as observed by N-terminal sequencing of the recombinant protein. The protein was then lyophilized, redissolved in water at 1-5 mg/ml, and stored in small aliquots at 80° C.

Larger amounts of the recombinant proteins, and in particular of CCL2-P8A, were obtained also by using an alternative protocol designed for purifications starting from the cell pellet obtained from large fermentation cultures of *E. coli* strains producing these proteins. Generally a 5 L fermentor produces approximately 200 g wet weight cell pellet, and a fermentor of 50 L produces 1.8 kg wet weight cell pellet. The purification procedure described here treats 200 g wet weight cell pellet.

The cell pellet was thawed and 3 ml of breakage buffer per gram wet weight (50 mM Tris/HCl buffer, pH 8.0 (Cat. 20092391, Biosolve) containing 10 mM MgCl2 (Cat. 63065, Fluka), 5 mM Benzamidine/HCl (Cat. 12073, Fluka), 1 mM 1,4 DL dithiothreitol (DTT) (Cat. 43819, Fluka), 1 mM phenylmethylsulfonyl fluoride (PMSF) (Cat. 78830, Fluka)* 20 mg/L DNase (Fluka) (Cat. DN-25, Sigma) was added. The suspension was homogenized with a Polytron to obtain a good homogenate devoid of fragments or clumps. All manipulations were carried out at 4° C. The homogenized bacterial suspension was transferred to a French Press cell mechanical disrupter (differential pressure). The number of passages was typically 2-4 under 1500 bar. The cell break was monitored by SDS-PAGE stained with Coomassie blue.

The lysate was dispensed into GSA centrifuge tubes and centrifuged at 10,000 rpm with the Sorval RC5C (16'300×g) for 90 minutes at 4° C. After centrifugation, the supernatant was discarded after confirmation by SDS-PAGE analysis that no soluble protein of interest could be detected in the supernatant. The pellet was removed with a spatula from the centrifuge tube and transferred it to a pre-weighed beaker to weigh the pellet. The pellet was washed with de-ionized water by adding 5 ml of water per gram of pellet in a beaker and stirred for 30 min at 4° C. with a magnetic stirrer. The suspension was centrifuged in GSA centrifuge tubes at 10,000 rpm with the Sorval RC5C centrifuge (16,300×g) for 60 min at 4° C. The wash step was repeated 3 times. After each centrifugation, the supernatant was discarded after confirmation by SDS-PAGE analysis that no soluble protein of interest could be detected in the supernatant.

The pellet was solubilised in inclusion body freshly prepared extraction buffer (100 mM Tris/HCl buffer, pH 8.0 (Cat. 20092391, Biosolve) containing 1 mM 1,4 DL dithiothreitol (DTT) (Cat. 43819, Fluka) and 6 M Guanidium/HCl (Cat. 50950, Fluka)) in a ratio of 100 ml of buffer for 25 g cell pellet using a Polytron. The solution was heated for 30 min at 60° C. and stirred to ensure monomerisation, then cooled to room temperature. The homogenate was dispensed into Ti45 centrifuge tubes and ultracentrifuged at 35,000 rpm with the Beckman L-60 (100,000×g). The supernatant was filtered with a 0.8-0.2 mm filter (SpiralCap (Cat. 12069, PALL), analyzed by SDS-PAGE and quantified using the Coomassie protein assay reagent (Pierce) following the protocol supplied with the kit.

The recombinant protein of interest is captured on a Fine-Line 35 Pilot column containing Source 30 RPC resin packed following the supplier's instructions (Amersham Pharmacia). After use, the column is regenerated following the cleaning procedure supplied by the manufacturer (Amersham Pharmacia). For 100 grams of cell pellet, a column of 3.5 cm diameter×23 cm height giving a total of 220 ml (equivalent to a 1 Column Volume) of Source 30 RPC is packed. The column was installed on an AKTA FPLC (Amersham Pharmacia). The flow rate was 10 ml/min, and the maximum pressure was 1 MPa. Before loading the sample the column was washed with deionised water for 2 Column Volume (440 ml). After washing, the column was equilibrated with 5 CVs (Column Volumes) of equilibration buffer (100 mM Tris/HCl buffer, (Cat. 20092391, Biosolve) adjusted to pH 7.5 with fuming 37% HCl (Cat 84426, Fluka).

The dissolved Ibs (Inclusion Bodies) in Guanidium/HCl were loaded onto the column at a flow rate of 5 ml/min. The column was then washed with 5 Column Volume of equilibration buffer followed by 5 CVs of buffer A (0.1% TFA Trifluoroacetic acid (Cat. 28904, Pierce) and 99.9% Distilled water). The protein is eluted using a linear gradient from 0% to 100% of buffer B (0.1% TFA Trifluoroacetic acid (Cat. 28904, Pierce) 9.9% distilled water, 90% Acetonitrile (UN1648, Baker), over 10 CV with a flow rate of 10 ml/min, and a 1 MPA pressure limit. 10 ml fractions were collected. All peaks detected were analysed by SDS-PAGE, HPLC and quantified by UV-spectroscopy. The fractions containing the protein of interest were pooled and the amount measured by UV-spectroscopy.

The protein was renatured by a 10-fold dilution into renaturation buffer (100 mM Tris/HCl buffer, pH 8.0 (Cat. 20092391, Biosolve) containing 0.1 mM Reduced Glutathione (Cat. G-4251, Sigma) and 0.01 mM Oxidised Glutathione (Cat. 120 000 250, Acros Organic) to obtain a final concentration of approximately 0.1 mg/ml. The pool of Source 30 RPC was added dropwise into the renaturation buffer. If the volume is large, this can be carried out using a peristaltic pump. The solution was stirred overnight at 4° C. The solution often appears cloudy due to the precipitation of protein that has not renatured. Final concentrations ranging from 0.1 to 0.4 mg/ml in the renaturation buffer yielded equivalent amounts of renatured protein (40 to 50%). The pH and acetonitrile in the starting material does not affect the renaturation step. Renaturation can be followed by HPLC to follow the refolding.

The renaturation solution was filtered using a High Flow peristaltic pump with a double filter, consisting of a prefilter of 0.8 mm followed by a 0.22 mm. The clarified solution was then concentrated by cation exchange on Hiload SP Sepharose HP after quantification by a UV-spectrum. The size of the ion exchange column depends of the amount of protein. For <500 milligrams, a 16/10 column (1 CV=20 ml) was used; 500-1000 mg, a 26/10 column (1 CV=50 ml) and for 1-2 grams, a 50/5 column (1 CV=100 ml).

The column was packed according to the supplier's instructions (Amersham Pharmacia). The column was washed with 2 CVs of deionised water, and then equilibrated with 4 CVs of cation exchange buffer A (50 mM Acetic acid (Fluka), adjusted to pH to 4.5 with NaOH (Cat. 71690 Fluka). The solution was adjusted to pH 4.5 with acetic acid and the conductivity adjusted to <10 mS. After loading the protein solution at the flow rate recommended by the supplier for the column chosen, the column was washed with 5 CVs of buffer A. The protein was eluted with a linear gradient from 0% to 100% of buffer B (buffer A, containing 2 M NaCl (Cat. 71380, Fluka) over 20 CVs. The fraction size was determined by the column size. All peaks detected were analysed by SDS-PAGE, HPLC and quantified by UV-spectroscopy. After analysis, the fractions containing AS900652 were pooled, quantified by UV-spectrum and analysed by HPLC.

The removal the N-terminal Methionine was performed enzymatically using Methionine Aminopeptidase (MAP), followed by a purification step. Briefly, the sample was first dialysed using membrane tubing with a cut-off of 3.5 kD into cleavage buffer (35 mM Tris/HCl buffer, pH 7.5 (Cat. 20092391, Biosolve). The dialysis buffer was changed three times over 24 hours. Methionine Aminopeptidase (MAP) was added to the protein solution at a ratio of 1:10000 (w:w, enzyme:protein). The digestion was performed at room temperature for 48 hours. The digested protein was then purified by cation exchange is carried out as described above. The protein was >98% pure as estimated by SDS-PAGE.

The AKTA purifier system (Pharmacia) was used to further purify the desired protein. The system was cleaned for 1 hour with 1 M NaOH, washed with sterile water, and equilibrated in buffer filtered with a 0.22 mm filter (0.1% TFA (Trifluoroacetic acid) (Cat. 28904, Pierce) 99.9% Distilled water). The protein was desalted using G-25 fine Sepharose XK50/30 column. The column was washed with 1 CV of 1 M NaOH followed by 4 CVs of sterile water and then equilibrated with 5 CVs 0.1% TFA. For optimal desalting conditions, 50- to 100 ml samples are desalted on the 450 ml G-25 fine Sepharose. For volumes larger than 100 ml, the desalting step is repeated. The sample was filtered with 0.22 mm filter before loading. The column is eluted with 1.5 CV 0.1% TFA with a flow rate of 10 ml/min and a maximum pressure of 1 MPa. Fractions of 10 ml are collected into sterile tubes. After analysis, the fractions containing the protein are pooled, quantified by UV-spectrum under sterile conditions and analysed by HPLC, SDS-PAGE and mass spectrometry.

The remaining contaminants are removed by using a preparative reverse phase chromatography (RPC) on DeltaPrep HPLC (WATERS). The sample was acidified to 0.1% TFA and loaded onto a Vydac C8 RPC (Cat. 208TB101522, Vydac) equilibrated in buffer A (0.1% TFA Trifluoroacetic acid (Cat. 28904, Pierce) and 99.9% distilled water). The protein was eluted using a linear gradient from 0% to 100% of buffer B (0.1% TFA Trifluoroacetic acid (Cat. 28904, Pierce), 99% Acetonitrile (UN1648, Baker), over 10 CV with a flow rate of 25 ml/min, and a 700 bar pressure limit. All peaks detected were analysed by SDS-PAGE, HPLC and quantified by UV-spectroscopy. After analysis, the fractions containing AS900652 were pooled, quantified by UV-spectrum, aliquoted as required and lyophilised. The protein is stored at −20° C. or −80° C.

The recombinant protein is quantified by UV spectroscopy using a UV-VIS spectrophotometer (Uvikon system, KONTRON). A quartz cuvette (QS 1.000, HELLMA) was used for the buffer reference and the other cuvette contains the sample. A scan from 350 nm to 240 nm was measured and the absorptions at 280 nm was used to determine the quantification according the extinction coefficient obtained from the amino acid composition using ProtParam, Expasy. The value used was 1.1 for a solution of 1 mg/ml for the oxidised protein containing disulfide bonds.

SDS-PAGE analyses were carried out using NuPAGE 10% gel (Cat. NP0301, Invitrogen). The sample was diluted 2 fold in sample buffer (cat. LC2676, Invitrogen) and heated for 5 minutes at 95° C. The Benchmark protein ladder was used as molecular weight standards. 10 µl of molecular weight standard solution and 20 µl of protein sample were loaded in the appropriate wells. The electrophoresis running buffer was MES (Cat. NP0002, Invitrogen). The migration was carried out according to the supplier's instructions of 200 V, 12 mA and 25 W for 35 minutes (PowerEase500, Invitrogen).

NuPAGE gels were stained with 0.1% R250 Coomassie blue in 10% acetic acid, 30% methanol in distilled water for 30 minutes, and de-stained in 10% acetic acid, 30% methanol in distilled water under slow rocking motion until background level is not coloured. The gel was then washed several times in water prior to embedding in drying solution (Invitrogen) sandwiched between two cellophane paper sheets (Invitrogen) for 10 minutes and then mounted in the miniature press allowing the gel to be stored as a fine sheet. Alternatively the gel was stained with the SimplyBlue Safe stain protocol (Cat. LC6065, Invitrogen).

The Alliance HPLC system supplied by WATERS was used with an analytical C8 Aquapore RP-300 7 m (0.2 cm diam.×22 cm) equilibrated in 0.1% TFA. 10-50 mg previously acidified 0.1% final TFA were injected. Proteins were eluted with a gradient of 25 to 50% acetonitrile over 20 CVs.

The identity of the recombinant protein was confirmed by mass spectral analyses and N-terminal sequence analysis The correct N-terminal sequence QPDAINAAVT was obtained for the purified material.

A mass of 8655 Da was obtained for the main species corresponding to the theoretical mass of the protein chain with 2 disulfide bonds. A second species with a mass lower by 17 Da was also observed corresponding to the modification of the N-terminal Glutamine residue into a pyroglutamic acid. The presence of this modification has no influence on the activity of the protein.

Example 2

Cell Based Assays

Materials and Methods

Assays for Chemokine-Induced Peritoneal Cellular Recruitment

Female Balb/C mice (Janvier, France) of 8 to 12 weeks were housed under normal animal holding conditions with a standard 12-h light/dark cycle and free access to food and water. Groups composed of 3-6 mice were injected intraperitoneally with 200 µl of saline (sterile LPS-free NaCl 0.9% (w/v) or of this solution containing CCL2 or CCL2-P8A at 10 µg per injection. For studies investigating the inhibitory effects of CCL2-P8A on CCL2-induced peritoneal cell recruitment, these molecules were administered intraperitoneally 30 minutes before the intraperitoneal injection of CCL2. All the molecules were administered at the concentration and in buffer above indicated (saline). The mice were sacrificed on at 4 hours after the CCL2 or CCL2-P8A final injection.

The assay for thioglycollate-induced peritoneal cell recruitment has been published (Mishell B, 1980). Briefly, thioglycollate medium was prepared by suspending 30 g of dehydrated thioglycollate medium (Becton Dickinson) in 1 liter of cold distilled water, then heated until boiling to dissolve the powder completely. The medium was then aliquoted into 100 ml bottles and autoclaved. After cooling, the medium was stored in the dark at room temperature for at least one month. Cellular recruitment was induced by intraperitoneal injection of mice in groups of 3 with 200 µl of a 3% solution of thioglycollate on Day 1, 30 minutes after CCL2*-P8A administration. CCL2* was administered daily thereafter for 3 days (Days 2, 3 and 4). Dexamethasone (Sigma) was used as a positive control and administered at 10 mg/kg intraperitoneally. The mice were sacrificed on Day 5.

Peritoneal lavages to assess cell recruitment in the previous assays were performed as follows. Mice were sacrificed by asphyxiation with rising concentrations of CO2 in a plexiglass box. Skin was cleaned with 70% ethanol. The outer layer of skin was removed, exposing the peritoneal membrane. The peritoneal cavity was ravaged 3 times with 5 ml ice cold PBS (phosphate buffered saline) and fluid was pooled in a 15 ml polystyrene Falcon tube (Becton Dickinson) on ice. Each lavage was accompanied with a light massage of the peritoneal cavity. Lavage fluid was centrifuged at 425×g, the supernatant discarded and the resultant cell pellet was resuspended by gentle multiple pipetting in 1 ml PBS. 10 µl cell suspension was stained with 90 µl trypan blue and total cell counts were enumerated with a Neubauer haemocytometer by counting 4 areas each of 1 $mm^2$. The mean of the 4 counts was taken, multiplied by the dilution factor of 10, and multiplied again by 10 to give the number of cells per µl, according to the directions for use accompanying the haemocytometer. Finally the total value was multiplied by 1000 (to equal 1 ml) to arrive at the total cell number recovered.

Results

Recombinant mature human CCL2/MCP-1 and the mutants called CCL2* and the corresponding obligate monomer mutants called CCL2-P8A and CCL2*-P8A (FIG. 1) were expressed in *E coli*.

The literature clearly shows that P8A mutation in CCL2 blocks the formation of CCL2 dimers, without affecting the binding to cells expressing the receptor or to a viral receptor-like protein, but also without showing the activities of a known CCL2 antagonist in relevant assays (see (1+9-76) MCP-1 in table I of Paaavola C D et al., 1998; Alexander J M et al., 2002)

The obligate monomeric form of CCL2 presents specific and unexpected properties in assays performed in cell-based assays. In the peritoneal cell recruitment assay, CCL2*-P8A and CCL2-P8A are unable to recruit cells compared with natural CCL2 (FIG. 2). Moreover, these molecules are able, in a dose dependent manner, to inhibit CCL2-induced (FIG. 3A) and thioglycollate-induced macrophage recruitment (FIG. 3B). In the latter assay, CCL2-P8A appears as effective as the positive control (dexamethasone, a known anti-inflammatory compound).

Example 3

CCL2-P8A Properties in Animal Models for Diseases

Materials and Methods

Ovalbumin-Induced Lung Inflammation Model

The ovalbumin-induced lung inflammation model was performed as published (Blyth D I et al., 1996). Groups of 6 mice were sensitised by an intraperitoneal injection of 10 µg chicken egg albumin precipitated in 2 mg aluminium hydroxide 2% (Serva) in a total volume of 200 µl, which were prepared by mixing 25 µl ovalbumin (2 mg/ml), 250 µl aluminium hydroxide in 725 µl LPS-free 0.9% NaCl (saline) and precipitated 3-4 hours at 4° C. Fifteen days after sensitisation, mice were treated and challenged in groups of 6 mice with the intranasal administration of 15 µg ovalbumin in 50 µl saline, under inhaled anaesthesia (Isoflurane) daily from day 15 to 19. CCL2-P8A (200 µl, 10 µg per intraperitoneal injection) was administered 30 minutes before each challenge. Peritoneal lavages to assess cell recruitment and cell counts were performed as described above in Example 2.

EAE (Experimental Autoimmune Encephalomyelitis) Model

C57Bl/6 mice from Charles River Italy (the selected strain has documented susceptibility to EAE; Sahrbacher U C et al., 1998.) are immunized (day=0) by injecting s.c. in the left flank 0.2 mL of an emulsion composed of 200 µg $MOG_{35-55}$ peptide (Neosystem, Strasbourg, France) in Complete Freund's Adjuvant (CFA, Difco, Detroit, U.S.A.) containing 0.5 mg of *Mycobacterium tuberculosis*. Immediately after, they receive an i.p. injection of 500 ng pertussis toxin (List Biological Lab., Campbell, Calif., U.S.A.) dissolved in 400∥L of buffer (0.5 M NaCl, 0.017% Triton X-100, 0.015 M Tris, pH=7.5). On day 2, the animals are given a second i.p. injection of 500 ng pertussis toxin. On day 7, the mice receive a second dose of 200 µg of $MOG_{35-55}$ peptide in CFA injected s.c. in the right flank. Starting approximately from day 8-10, this procedure results in a gradually progressing paralysis, arising from the tail and ascending up to the forelimbs. Starting from day 7 the animals are individually examined for the presence of paralysis by means of a clinical score as follows:
0=no sign of disease
0.5=partial tail paralysis
1=tail paralysis
1.5=tail paralysis+partial unilateral hindlimb paralysis
2=tail paralysis+hindlimb weakness or partial hindlimb paralysis
2.5=tail paralysis+partial hindlimb paralysis (lowered pelvi)
3=tail paralysis+complete hindlimb paralysis
3.5=tail paralysis+complete hindlimb paralysis+incontinence
4=tail paralysis+hindlimb paralysis+weakness or partial paralysis of forelimbs
5=moribund or dead The treatment with compounds or vehicle starts for each animal at day 7 post immunization and is continued for 21 consecutive days (10-12 animals per treatment group). Interferon beta and CCL2-P8A were administered s.c. or i.p., respectively, once a day solubilized in 10 ml/kg PBS at the doses indicated in the figure.

Delayed Contact Hypersensitivity Model

The mouse ear-swelling test to measure contact hypersensitivity was performed as previously described (Garrigue J L et al., 1994). Briefly, mice were pre-sensitized topically by applying 25 µl of 0.5% 2,4-dinitrofluorobenzene (DNFB; Sigma Chemical Co.) solution in acetone/olive oil (4:1) to the shaved abdomen. Five days later, 20 µl of 0.2% DNFB in the same vehicle was applied to the right ears, and vehicle alone to the left ears. Mice (n=6 per group) were treated daily on Day 5 with an intraperitoneal administration of 0.05, 0.5 or 5 mg/kg (1, 10 or 100 micrograms/mouse, respectively) of CCL2-P8A, Dexamethasone (1 mg/kg), or PBS only in the control group. The treatment was administered 30 minutes prior to the DNFB challenge. Ear thickness was measured with a dial thickness gauge (Mitutoyo Corp.), Ear swelling was estimated by subtracting the pre-challenge from the post-challenge value, and by further subtracting any swelling detected in the vehicle-challenged contralateral ear.

Results

The potential therapeutic activities of CCL2-P8A as chemokine antagonist have been tested in animal models for inflammatory and autoimmune diseases.

Figure 4:
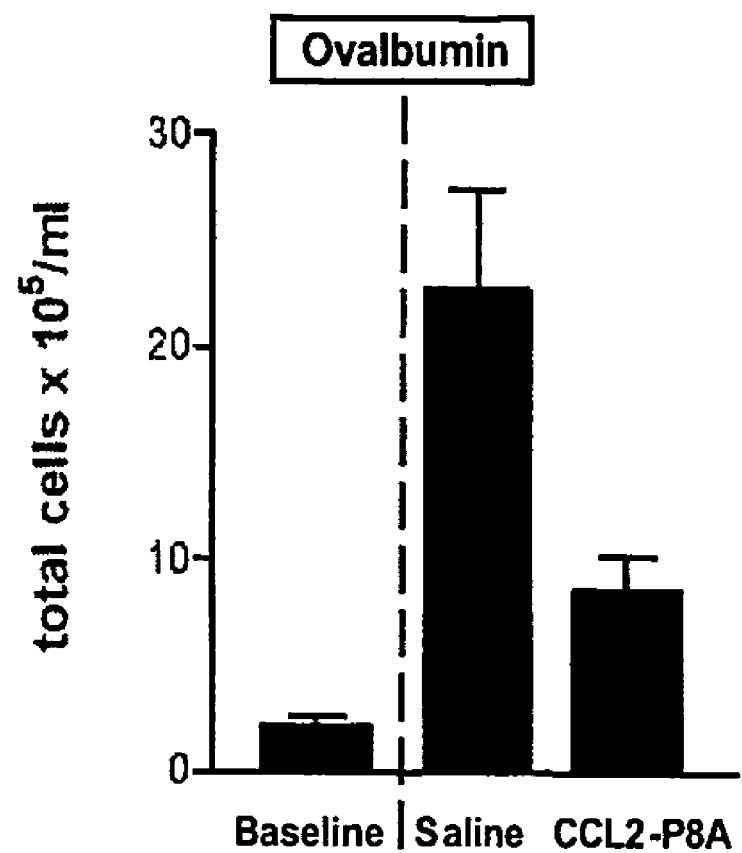

CCL2*-P8A was tested in a disease model, the ovalbumin-induced lung inflammation. In this classic model for allergic lung inflammation, the mice are sensitised with ovalbumin, with an adjuvant of aluminium hydroxide during sensitisation phase to boost the immune response, and then challenged by intranasal administration of ovalbumin over a period of 5 consecutive days, wherein CCL2-P8A was administered intraperitoneally throughout this phase. Also in this case, CCL2-P8A was capable to inhibit cell recruitment (FIG. 4).

In a second model, CCL2-P8A was tested in the EAE (Experimental Autoimmune Encephalomyelitis) model, a well known model for multiple sclerosis that has been used to validate antagonists of chemokines (including CCL2) for the treatment of this autoimmune, inflammatory demyelinating disease of the human central nervous system (Mahad D J and Ransohoff R M, 2003; Izikson L et al., 2002). CCL-P8A was tested in animals showing either mild or severe level of the disease, as evaluated by clinical score, following the treatment of the EAE-inducing compounds. Each of the two groups of animals were divided in five subgroups: three of them were treated with different amounts of CCL2-P8A, and the two others were used as either negative control (treated with vehicle only) or as positive control (treated with Interferon-beta, a common therapeutic product for the treatment of multiple sclerosis). The evolution of the state of the animals was compared on the basis of the clinical score measured during the treatment period (21 days). In both disease models, the administration of CCL2-P8A (at a dosage down to 0.15 mg/kg) improves the state of the animals in a statistically significant manner. The observed decrease of the clinical score using CCL-P8A is at least comparable to that observed when interferon beta is used as treatment (FIG. 5).

Figure 6:
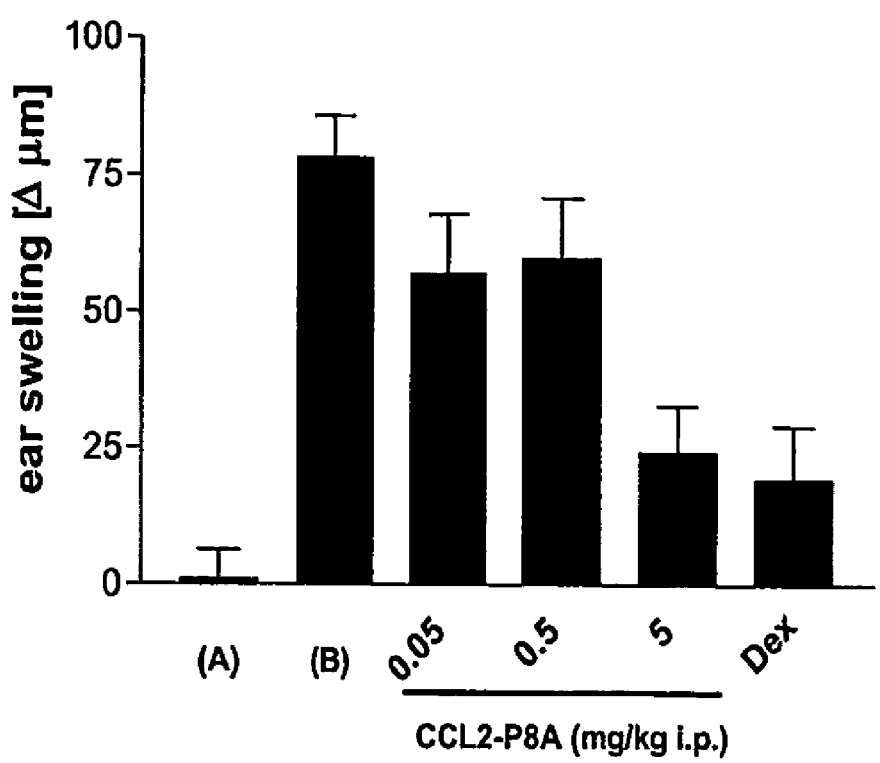

Another disease model, the contact hypersensitivity model was used to evaluate the potential therapeutic efficacy of CCL2-P8A on skin inflammation mediated by T cells. Contact hypersensitivity (CHS) is a Langerhans cell (LC)-dependent, T cell-mediated cutaneous immune response, reflecting a culmination of LC activities in vivo (uptake of epicutaneous antigens, migration into lymph nodes, and presentation of antigens to naive T cells). The model is well established for characterization of compound for dermatological indications like psoriasis and allergic contact dermatitis (Xu H et al. 1996). It involves a sensitisation phase and a subsequent challenge with an antigen, resulting in a skin inflammation with formation of edema and cellular infiltrates in the skin. The edema can be measured by caliper at the challenged site (ear of the mice). The involvement of chemokines, and of CCL2 in particular, in the development of this excessive response disease have been demonstrated (Mitsui G et al., 2003; Mizumoto N et al., 2001). Intraperitoneal administration of CCL2-P8A 30 minutes before a challenge with the antigen (DNFB, in this case) results in a decrease of the swelling comparable to that observed using a known anti-inflammatory compound (Dexamethasone) one day after the treatment. Control mice were obtained by challenging them with the antigen, but with or without previous sensitisation, so that T cell dependent inflammation and edema is formed or not (FIG. 6).

Therefore, a monomeric variant of a homodimer-forming CC-chemokine, wherein said variant result from at least an amino acid substitution that alters the pattern of hydrogen bonds at the dimerization interface, are inhibitors of chemokine-mediated cell recruitment in in vivo cell recruitment assays as well as in animal models for human diseases, implying that this is a novel strategy for generating chemokine variants which can be used for preparing pharmaceutical compositions and in therapeutic methods.

Example 4

Alternative Forms of CCL2-P8A

Alternative forms of the chemokine variants disclosed above can be generate d by introducing mutations known in the art as improving specific features.

One or more single amino acid substitutions and/or additions can be introduced in different position of CCL2-P8A (FIG. 7A). CCL2-P8A can be expressed as a mature protein missing the natural Glutammine N-terminal residue, or by adding an additional small residue (such as Alanine or Glycine) at the N-terminus before Glutamine, so that this residue does not remain exposed and does not get converted spontaneously into the pryoglutamate form (Gong J and Clark-Lewis I, 1995). CCL-P8A can also be mutated in way that a fifth Cysteine is available to allow specific PEGylation reactions. These PEGylation sites can be integrated at the level of either an internal amino acid (for example at Asparagin 14 or 17, and even at position 8, so that a single modification can allow both monomerization and PEGylation) or of the C-terminus (by directly adding a Cysteine after the natural C-terminal Threonine).

A further variant of CCL2-P8A can be obtained by fusing this sequence to an immunoglobulin domain constant region, a protein domain known to improve the stability and the efficacy of recombinant proteins in the circulation. The resulting fusion protein can be expressed directly by mammalian cells (such as CHO or HEK293 cells) using the appropriate expression vectors so that the fusion protein is secreted in the culture medium. In a preferred arrangement, the nucleic acid sequence encoding the mature CCL2-P8A can be cloned in an expression vector fused to a nucleic acid sequence encoding the human CCL2 signal sequence at its 5' end, and the nucleic acid sequence encoding the constant region (segment 246-467) of human immunoglobulin lambda heavy chain IgG1 (NCBI Acc. No. CAA75302) at its 3' end. The resulting vector can be used to transform a CHO or HEK293 cell line and the clones stably expressing and secreting the recombinant fusion protein having CCL2-P8A at the N-terminus and the IgG1 sequence at the C-terminus (FIG. 7B) can be selected. This clone then can be used for scaling up the production and for purifying the recombinant fusion protein from the culture medium. Alternatively, the position of the nucleic acid encoding the constant region (segment 243-474) of human immunoglobulin lambda heavy chain IgG1 and CCL2-P8A can be inversed, and the resulting protein can be expressed and secreted using still the human CCL2 signal sequence, or any other signal sequence.

TABLE I

| Amino Acid | Synonymous Groups | More Preferred Synonymous Groups |
|---|---|---|
| Ser | Gly, Ala, Ser, Thr | Thr, Ser |
| Arg | Asn, Lys, Gln, Arg, His | Arg, Lys, His |
| Leu | Phe, Ile, Val, Leu, Met | Ile, Val, Leu, Met |
| Pro | Pro, Ala, Ser, Thr | Pro |
| Thr | Gly, Ala, Ser, Thr | Thr, Ser |
| Ala | Gly, Thr, Ser | Gly, Ala |
| Val | Met, Phe, Ile, Leu, Val | Met, Ile, Val, Leu |
| Gly | Ala, Thr, Ser, Gly | Gly, Ala |
| Ile | Phe, Ile, Val, Leu, Met | Ile, Val, Leu, Met |
| Phe | Trp, Phe, Tyr | Tyr, Phe |
| Tyr | Trp, Phe, Tyr | Phe, Tyr |
| Cys | Ser, Thr, Cys | Cys |
| His | Asn, Lys, Gln, Arg, His | Arg, Lys, His |
| Gln | Glu, Asn, Asp, Gln | Asn, Gln |
| Asn | Glu, Asn, Asp, Gln | Asn, Gln |
| Lys | Asn, Lys, Gln, Arg, His | Arg, Lys, His |
| Asp | Glu, Asn, Asp, Gln | Asp, Glu |
| Glu | Glu, Asn, Asp, Gln | Asp, Glu |
| Met | Phe, Ile, Val, Leu, Met | Ile, Val, Leu, Met |
| Trp | Trp, Phe, Tyr | Trp |

TABLE II

| Amino Acid | Synonymous Group |
|---|---|
| Ser | D-Ser, Thr, D-Thr, allo-Thr, Met, D-Met, Met(O), D-Met(O), L-Cys, D-Cys |
| Arg | D-Arg, Lys, D-Lys, homo-Arg, D-homo-Arg, Met, Ile, D-.Met, D-Ile, Orn, D-Orn |
| Leu | D-Leu, Val, D-Val, AdaA, AdaG, Leu, D-Leu, Met, D-Met |
| Pro | D-Pro, L-I-thioazolidine-4-carboxylic acid, D-or L-1-oxazolidine-4-carboxylic acid |
| Thr | D-Thr, Ser, D-Ser, allo-Thr, Met, D-Met, Met(O), D-Met(O), Val, D-Val |
| Ala | D-Ala, Gly, Aib, B-Ala, Acp, L-Cys, D-Cys |
| Val | D-Val, Leu, D-Leu, Ile, D-Ile, Met, D-Met, AdaA, AdaG |
| Gly | Ala, D-Ala, Pro, D-Pro, Aib, .beta.-Ala, Acp |
| Ile | D-Ile, Val, D-Val, AdaA, AdaG, Leu, D-Leu, Met, D-Met |
| Phe | D-Phe, Tyr, D-Thr, L-Dopa, His, D-His, Trp, D-Trp, Trans-3,4, or 5-phenylproline, AdaA, AdaG, cis-3,4, or 5-phenylproline, Bpa, D-Bpa |
| Tyr | D-Tyr, Phe, D-Phe, L-Dopa, His, D-His |
| Cys | D-Cys, S-Me-Cys, Met, D-Met, Thr, D-Thr |
| Gln | D-Gln, Asn, D-Asn, Glu, D-Glu, Asp, D-Asp |
| Asn | D-Asn, Asp, D-Asp, Glu, D-Glu, Gln, D-Gln |
| Lys | D-Lys, Arg, D-Arg, homo-Arg, D-homo-Arg, Met, D-Met, Ile, D-Ile, Orn, D-Orn |
| Asp | D-Asp, D-Asn, Asn, Glu, D-Glu, Gln, D-Gln |
| Glu | D-Glu, D-Asp, Asp, Asn, D-Asn, Gln, D-Gln |
| Met | D-Met, S-Me-Cys, Ile, D-Ile, Leu, D-Leu, Val, D-Val |

REFERENCES

Alexander J M et al., Cell, 111; 343-356, 2002.
Baggiolini M et al., Annu Rev Immunol, 15: 675-705, 1997.
Baggiolini M, J Intern Med, 250: 91-104, 2001.
Blyth D I et al., Am J Respir Cell Mol Biol., 14: 425-438, 1996.
Brown A et al., J Pept Sci 2:40-46, 1996.
Cleland J L et al., Curr Opin Biotechnol,12: 212-219, 2001.
Coleman R A et al., Drug Disc Toay, 6:1116-1126, 2001.
Dougherty D A, Curr Opin Chem Bio, 4: 645-652, 2000.
Fernandez E J and Lolis E, Annu Rev Pharmacol Toxicol, 42:469-499, 2002.
Garrigue J L et al., Contact Dermatitis, 30: 231-237, 1994.
Godessart N and Kunkel S L, Curr Opin Immunol, 13: 670-675, 2001.
Golebiowski A et al., Curr Opin Drug Discov Devel, 4: 428-434, 2001.
Gong J and Clark-Lewis I, J Exp Med 181: 631-640, 1995.
Gosling J et al., J Clin Invest, 103: 773-778, 1999.
Greenwald R B et al., Adv Drug Deliv Rev, 55: 217-50, 2003.
Gu L et al., Chem Immunol, 72: 7-29, 1999.
Gu L et al., Nature, 404: 407-411, 2000.
Harris J M and Chess R B, Nat Rev Drug Discov, 2: 214-21, 2003.
Handel T et al., Biochemistry, 35: 6569-4584, 1996.
Hemmerich S et al., Biochemistry, 38: 13013-13025, 1999.
Hruby V J and Balse P M, Curr Med Chem, 7:945-970, 2000.
Izikson L et al., Clin Immunol, 103: 125-31 2002.
Kim K S et al., FEBS Lett, 395:277-282, 1996.
Li A P, Drug Disc Today, 6: 357-366, 2001
Loetscher P and Clark-Lewis I, J Leukoc Biol, 69: 881-884, 2001.
Lu B et al., J Exp Med, 187: 601-608, 1998.
Lubkowski J et al., Nat Struct Biol, 4: 64-69, 1997.
Luo B and Prestwich G D, Exp Opin Ther Patents, 11: 1395-1410, 2001.
Mishell B, Immunopharm, 2: 233-245, 1980.
Mahad D J and Ransohoff R M, Semin Immunol, 15: 23-32, 2003.
Mitsui G et al., Immunol Lett, 86: 191-7, 2003.
Mizumoto N et al., Immunobiology, 204:477-93, 2001.
Murphy L R et al., Protein Eng, 13:149-152, 2000.
Nilsson J et al., Protein Expr Purif, 11: 1-16, 1997.
Paavola C et al., J Biol Chem, 273: 33157-33165, 1998.
Pillai O and Panchagnula R, Curr Opin Chem Biol, 5: 447-451, 2001.
Proudfoot A et al., Proc Natl Acad Sci USA, 100: 1885-1890, 2003.
Rogov S I and Nekrasov A N, Protein Eng, 14: 459-463, 2001.
Sahrbacher U C et al., Eur J Immunol, 28: 1332-8, 1998.
Schwarz M K and Wells T N, Curr Opin Chem Biol, 3: 407-417, 1999.
Seet B T et al., Proc Natl Acad Sci USA, 98: 9008-9013, 2001.
Steitz S A et al., FEBS Lett, 430: 158-164, 1998.
Villain M et al., Chem Biol, 8: 673-679, 2001.
Yoshimura T et al., FEBS Lett, 244: 487-493, 1989.
Xu H et al., J Exp Med, 183: 1001-12, 1996.
Zhang Y et al., Methods, 10: 93-103, 1996.

The invention claimed is:

1. A method for treating an autoimmune or inflammatory disease comprising the administration of an effective amount of a monomeric variant to an individual having an autoimmune or inflammatory disease,
   wherein Monocyte Chemoattractant Protein 1 (MCP-1) signaling is involved in the autoimmune or inflammatory disease process and said monomeric variant comprises:
   a) SEQ ID NO: 2 (CCL2-P8A);
   b) SEQ ID NO: 4 (CCL2*-P8A):
   c) SEQ ID NO: 2 or SEQ ID NO: 4 with the substitution of a Cysteine in position 8, 14 or 17;
   d) SEQ ID NO: 2 or SEQ ID NO: 4 with the substitution of an Alanine or a Glycine in position 1; or
   e) SEQ ID NO: 2 or SEQ ID NO: 4 with the addition of a Cysteine at the C-terminus.

2. The method according to claim 1, wherein said monomeric variant comprises SEQ ID NO: 2.

3. The method according to claim 1, wherein said monomeric variant comprises SEQ ID NO: 4.

4. The method according to claim 1, wherein said monomeric variant contains a Cysteine in position 8, 14 or 17 of SEQ ID NO: 2.

5. The method according to claim 1, wherein said monomeric variant further comprises a constant region of a human immunoglobulin heavy chain.

6. The method according to claim 1, wherein the disease is multiple sclerosis.

7. The method according to claim 1, wherein said monomeric variant comprises SEQ ID NO: 2 and said autoimmune or inflammatory disease is multiple sclerosis.

8. The method according to claim 1, wherein said monomeric variant comprises SEQ ID NO: 2 and an additional Cysteine at the C-terminus.

9. The method according to claim 1, wherein said monomeric variant comprises SEQ ID NO: 4 and an additional Cysteine at the C-terminus.

10. The method according to claim 1, wherein said monomeric variant contains an Alanine or a Glycine in position 1 of SEQ ID NO: 2.

11. The method according to claim 1, wherein said monomeric variant contains an Alanine or a Glycine in position 1 of SEQ ID NO: 4.

12. The method according to claim 1, wherein said monomeric variant contains a Cysteine in position 8, 14 or 17 of SEQ ID NO: 4.

* * * * *

UNITED STATES PATENT AND TRADEMARK OFFICE
CERTIFICATE OF CORRECTION

PATENT NO. : 7,740,833 B2  Page 1 of 2
APPLICATION NO. : 10/573625
DATED : June 22, 2010
INVENTOR(S) : Amanda Proudfoot, Jeffrey Shaw and Zoe Johnson It is certified that error appears in the above-identified patent and that said Letters Patent is hereby corrected as shown below:

Column 2,
Line 13, "relate d to" should read --related to--.
Line 18, "even though has been" should read --even though it has been--.

Column 5,
Line 45, "results altered" should read --results are altered--.

Column 10,
Line 17, "derived form" should read --derived from--.

Column 13,
Lines 10-12, "fatty oils, for example, sesame oil, or synthetic fatty acid esters, for example, sesame oil, or synthetic fatty acid esters, for example, ethyl" should read --fatty oils, for example, sesame oil, or synthetic fatty acid esters, for example, ethyl--.

Column 15,
Line 60, "transferred it to" should read --transferred to--.

Column 17,
Line 1, "depends of the" should read --depends on the--.
Line 9, "adjusted to pH to 4.5" should read --adjusted to pH 4.5--.
Line 31, "exchange is carried out" should read --exchange and carried out--.

Column 19,
Line 26, "was ravaged" should read --was lavaged--.
Line 55, "Paaavola" should read --Paavola--.

Column 20,
Line 33, "400 ‖ L" should read --400 µL--.

Signed and Sealed this

Twelfth Day of October, 2010

David J. Kappos
*Director of the United States Patent and Trademark Office*

Column 22,
Line 37, "mutated in way that" should read --mutated in a way that--.

Column 24,
Line 22, "6569-4584" should read --6569-6584--.

SEQUENCE LISTING

<160> NUMBER OF SEQ ID NOS: 5

<210> SEQ ID NO 1
<211> LENGTH: 76
<212> TYPE: PRT

<213> ORGANISM: Homo sapiens
<220> FEATURE:
<223> OTHER INFORMATION: Human CCL2

<400> SEQUENCE: 1

Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
    50                  55                  60

Asp His Leu Asp Lys Gln Thr Gln Thr Pro Lys Thr
65                  70                  75

<210> SEQ ID NO 2
<211> LENGTH: 76
<212> TYPE: PRT
<213> ORGANISM: Artificial sequence
<220> FEATURE:
<223> OTHER INFORMATION: Human CCL2-P8A

<400> SEQUENCE: 2

Gln Pro Asp Ala Ile Asn Ala Ala Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
    50                  55                  60

Asp His Leu Asp Lys Gln Thr Gln Thr Pro Lys Thr
65                  70                  75

<210> SEQ ID NO 3
<211> LENGTH: 76
<212> TYPE: PRT
<213> ORGANISM: Artificial sequence
<220> FEATURE:
<223> OTHER INFORMATION: Human CCL2*

<400> SEQUENCE: 3

Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Ile
    50                  55                  60

Asp His Leu Asp Lys Gln Thr Gln Thr Pro Lys Thr
65                  70                  75

<210> SEQ ID NO 4
<211> LENGTH: 76
<212> TYPE: PRT
<213> ORGANISM: Artificial sequence
<220> FEATURE:
<223> OTHER INFORMATION: Human CCL2*-P8A

<400> SEQUENCE: 4

```
Gln Pro Asp Ala Ile Asn Ala Ala Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Ile
50                  55                  60

Asp His Leu Asp Lys Gln Thr Gln Thr Pro Lys Thr
65                  70                  75
```

<210> SEQ ID NO 5
<211> LENGTH: 331
<212> TYPE: PRT
<213> ORGANISM: Artificial sequence
<220> FEATURE:
<223> OTHER INFORMATION: Human CCL2-P8A_IgG1 fusion protein

<400> SEQUENCE: 5

```
Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Ala Val
            20                  25                  30

Thr Cys Cys Tyr Asn Phe Thr Asn Arg Lys Ile Ser Val Gln Arg Leu
        35                  40                  45

Ala Ser Tyr Arg Arg Ile Thr Ser Ser Lys Cys Pro Lys Glu Ala Val
50                  55                  60

Ile Phe Lys Thr Ile Val Ala Lys Glu Ile Cys Ala Asp Pro Lys Gln
65                  70                  75                  80

Lys Trp Val Gln Asp Ser Met Asp His Leu Asp Lys Gln Thr Gln Thr
                85                  90                  95

Pro Lys Thr Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Asn Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Gln Gly Gln Pro Glu
            260                 265                 270

Asn Asn Tyr Lys Thr Thr Pro Pro Val Leu Asp Ser Asp Gly Ser Phe
```

-continued

```
            275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330
```